(12) United States Patent
Greene et al.

(10) Patent No.: US 7,179,785 B2
(45) Date of Patent: Feb. 20, 2007

(54) COMPOUNDS THAT BIND TO P185 AND METHODS OF USING THE SAME

(75) Inventors: Mark I. Greene, Penn Valley, PA (US); Ramachandran Murali, Swartmore, PA (US); Alan Berezov, Glenolden, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/301,499

(22) Filed: Nov. 21, 2002

(65) Prior Publication Data

US 2003/0148932 A1 Aug. 7, 2003

Related U.S. Application Data

(60) Provisional application No. 60/331,935, filed on Nov. 21, 2001.

(51) Int. Cl.
*A61K 38/00* (2006.01)

(52) U.S. Cl. .......................... 514/2; 424/1.69; 530/326; 530/327

(58) Field of Classification Search .................. 514/9, 514/14, 17, 44
See application file for complete search history.

(56) References Cited

U.S. PATENT DOCUMENTS

| | | | |
|---|---|---|---|
| 5,637,677 A | | 6/1997 | Greene et al. |
| 5,663,144 A | * | 9/1997 | Greene et al. ................ 514/14 |
| 6,100,377 A | | 8/2000 | Greene |
| 6,417,168 B1 | * | 7/2002 | Greene et al. ................ 514/44 |

FOREIGN PATENT DOCUMENTS

WO    WO 99/44645    9/1999

OTHER PUBLICATIONS

Online–Medical Dictionary. "Amino acid". http://cancer-web.ncl.ac.uk/cgi–bin/omd?query=amino+acid. Nov. 13, 1997.*
Di Blasio et al., (1993) "Noncoded Residues as Building Blocks in the Design of Specific Secondary Structures: Symmetrically Disubstituted Glycines and β–Alanine", *Biopolymers*, 1037–1049.
Frieden et al. (1980) "Adenosine Deaminase and Adenylate Deaminase: Comparative Kinetic Studies with Transition State and Ground State Analogue Inhibitors", *Biochemistry*, 19:5303–5309.
V. Hruby (1993) "Conformational and Topographical Consideration in the Design of Biologically Active Peptides", *Biopolymers*, 33:1073–1082.
Igarashi et al,. (1995) "Specific Binding of a Synthetic Peptide Derived from an Antibody Complementarity Determining Region to Phosphatidylserine", *J. Biochem.*, 117:452–457.
Laune et al., (1997) "Systematic Exploration of the Antigen Binding Activity of Synthetic Peptides Isolated from the Variable Regions of Immunoglobulins", *The Journal of Biol. Chemistry*, 272:30937–30944.
Leysen and Gommeren (1984) "The dissociation rate of unlabelled dopamine antagonists and agonists from the dopamine–$D_2$ receptor, application of an original filter method", *J. of Receptor Research*, 4:817–845.
Lodato et al., (1990) "Immunohistochemical Evaluation of c–erbB–2 Oncogene Expression in Ductal Carcinoma In Situ and Atypical Ductal Hyperplasia of the Breast", *Modern Pathology*, 3:449–454.
Manning et al., (1993) "Design of cyclic and linear peptide antagonists of vasopressin and oxytocin: current status and future directions", *Regulatory Peptides*, 45:279–283.
Markgren et al., "Kinetic Analysis of the Interaction between HIV–1 Protease and Inhibitors Using Optical Biosensor Technology", *Analytical Biochemistry*, 279:71–78.
Matsuyama et al., (1992) "A Novel Extracellular Cyclic Lipopeptide Which Promotes Flagellum–Dependent and—Independent Spreading Growth of *Serratia marcescens*", *J. of Bacteriology*, 174:1769–1776.
McGrath et al., (1997) "Crystal structure of human cathepsin K complexed with a potent inhibitor", *Nature Structural Biology*, 4:105–109.
Meyer et al., (1995) "Backward binding and other structural surprises", *Perspectives in Drug Discovery and Design*, 3:168–195.
Padlan et al., (1989) "Structure of an antibody–antigen complex: Crystal structure of the HyHEL–10 Fab–lysozyme complex", *Proc. Natl. Acad. Sci. USA*, 86:5938–5942.
Pargellis et al., (1994) "Determination of Kinetic Rate Constants for the Binding of Inhibitors to HIV–1 Protease and for the Association and Dissociation of Active Homodimer", *Biochemistry*, 33:12527–12534.

(Continued)

Primary Examiner—Cecilia J. Tsang
Assistant Examiner—Maury Audet
(74) *Attorney, Agent, or Firm*—Darby & Darby

(57) ABSTRACT

Novels peptides and pharmaceutical compositions comprising the same are disclosed. Conjugated compositions peptides linked to detectable agents and/or cytotoxic agents. are disclosed. Method of detecting tumors that have p185 on tumor cell surfaces are disclosed. Methods of preventing transformation of a normal cell into a tumor cell in an individual at risk of developing a tumor having tumor cells which have p185 on their surfaces are disclosed. Methods of treating an individual who has cancer characterized by tumor cells that have a p185 on their cell surfaces are disclosed.

22 Claims, 7 Drawing Sheets

(4 of 7 Drawing Sheet(s) Filed in Color)

OTHER PUBLICATIONS

Park et al., (2000) "Rationally designed anti–HER2/neu peptide mimetic disables P185$^{HER2/neu}$ tyrosine kinases in vitro and in vivo", *Nature Biotechnology*, 18:194–198.

Ripka and Rich (1998) "Peptidomimetic design", *Current Opinion of Chemical Biology*, 2:441–452.

Saragovi et al., (1991) "Design and Synthesis of a Mimetic from an Antibody Complementarity–Determining Region", *Science*, 253:792–795.

Saragovi and Greene (1992) "Constrained Peptides and Mimetics as Probes of Protein Secondary Structure" *Immunomethods*, 1:5–9.

Sautel et al., (1996) "Neuropeptide Y and the Nonpeptide Antagonist BIBP 3226 Share an Overlapping Binding Site at the Human $Y_1$ Receptor", *Molecular Pharmacology*, 50:285–292.

T. Schwartz (1994) "Locating ligand–binding sites in 7TM receptors by protein engineering", *Current Opinion in Biotechnology*, 5:434–444.

Sheriff et al., (1987) "Three–dimensional structure of an antibody–antigen complex", *Proc. Natl. Acad. Sci. USA*, 84:8075–8079.

Sliwkowski et al., (1999) "Nonclinical Studies Addressing the Mechanism of Action of Trastuzumab (Herceptrin)" *Seminars in Oncology*, 26(suppl. 12):60–70.

Thompson et al., (1997) "Design of potent and selective human cathepsin K inhibitors that span the active site", *Proc. Natl. Acad. Sci. USA*, 94:14249–14254.

Turk et al., (1995) "Crystal Structure of Cathepsin B Inhibited with CA030 at 2.0–Å Resolution: A Basis for the Design of Specific Epoxysuccinyl Inhibitors", *Biochemistry*, 34:4791–4797.

L. Weiner (1999) "An Overview of Monoclonal Antibody Therapy of Cancer", *Seminars in Oncology*, 26(suppl. 12):41–50.

Wood and Wetzel (1992) "Novel cyclization chemistry especially suited for biologically derived, unprotected peptides", *Int. J. Peptide Protein –Res.*, 39:533–539.

Yamamoto et al., (1991) "Refined X–ray Structure of Papain–E–64–c Complex at 2.1–Å Resolution", *The Journal of Biological Chemistry*, 266:14771–14777.

Yamashita et al., (1997) "Structure and Design of Potent and Selective Cathepsin K Inhibitors", *J. Am Chem. Soc.*, 119:11351–11352.

* cited by examiner

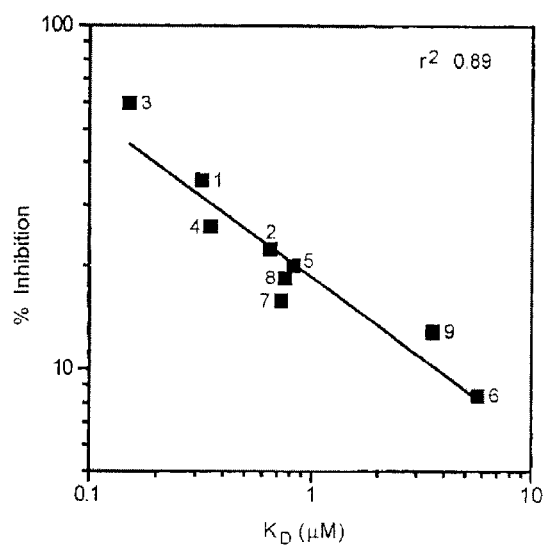
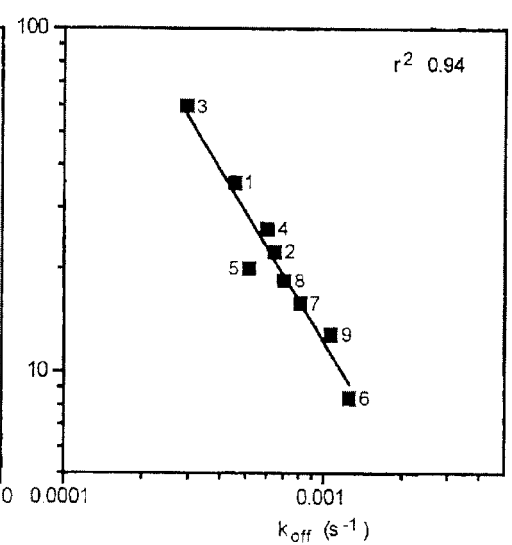
FIG. 6A
FIG. 6B

Time, min 30 min post injection

Tumor 90 min post injection

SEQUENCE LISTING

<160> NUMBER OF SEQ ID NOS: 152

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Gly Gly Gly Phe
1

<210> SEQ ID NO 2
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(4)
<223> OTHER INFORMATION: where Xaa is dPhe

<400> SEQUENCE: 2

Gly Gly Gly Xaa
1

<210> SEQ ID NO 3
<211> LENGTH: 4
<212> TYPE: PRT
<213> ORGANISM: Artificial Sequence
<220> FEATURE:
<223> OTHER INFORMATION: synthetic peptide

<400> SEQUENCE: 3

Gly Gly Gly Tyr
1

<210> SEQ ID NO 4
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(4)
<223> OTHER INFORMATION: where Xaa is dTyr

<400> SEQUENCE: 4

Gly Gly Gly Xaa
1

<210> SEQ ID NO 5
<211> LENGTH: 4
<212> TYPE: PRT
<213> ORGANISM: Artificial Sequence
<220> FEATURE:
<223> OTHER INFORMATION: synthetic peptide

<400> SEQUENCE: 5

Ser Gly Gly Phe
1

<210> SEQ ID NO 6

```
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(4)
<223> OTHER INFORMATION: where Xaa is dPhe

<400> SEQUENCE: 6

Ser Gly Gly Xaa
1

<210> SEQ ID NO 7
<211> LENGTH: 4
<212> TYPE: PRT
<213> ORGANISM: Artificial Sequence
<220> FEATURE:
<223> OTHER INFORMATION: synthetic peptide

<400> SEQUENCE: 7

Ser Gly Gly Tyr
1

<210> SEQ ID NO 8
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(4)
<223> OTHER INFORMATION: where Xaa is dTyr

<400> SEQUENCE: 8

Ser Gly Gly Xaa
1

<210> SEQ ID NO 9
<211> LENGTH: 5
<212> TYPE: PRT
<213> ORGANISM: Artificial Sequence
<220> FEATURE:
<223> OTHER INFORMATION: synthetic peptide

<400> SEQUENCE: 9

Asp Gly Phe Tyr Ala
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic peptide

<400> SEQUENCE: 10

Asp Gly Tyr Tyr Ala
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic peptide
```

```
<400> SEQUENCE: 11

Asp Gly Trp Tyr Ala
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic peptide

<400> SEQUENCE: 12

Asp Gly His Tyr Ala
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: where Xaa is dPhe

<400> SEQUENCE: 13

Asp Gly Xaa Tyr Ala
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: where Xaa is dTyr

<400> SEQUENCE: 14

Asp Gly Xaa Tyr Ala
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: where Xaa is dTrp

<400> SEQUENCE: 15

Asp Gly Xaa Tyr Ala
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
```

<223> OTHER INFORMATION: where Xaa is dHis

<400> SEQUENCE: 16

Asp Gly Xaa Tyr Ala
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: where Xaa is dAla

<400> SEQUENCE: 17

Asp Gly Phe Tyr Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: where Xaa is dAla

<400> SEQUENCE: 18

Asp Gly Tyr Tyr Xaa
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: where Xaa is dAla

<400> SEQUENCE: 19

Asp Gly Trp Tyr Xaa
1               5

<210> SEQ ID NO 20
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: where Xaa is dAla

<400> SEQUENCE: 20

Asp Gly His Tyr Xaa
1               5

<210> SEQ ID NO 21
<211> LENGTH: 5
<212> TYPE: PRT

```
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dPhe
<220> FEATURE:
<221> NAME/KEY: MISC_FEATURE
<222> LOCATION: (5)..(5)
<223> OTHER INFORMATION: where Xaa is dAla

<400> SEQUENCE: 21

Asp Gly Xaa Tyr Xaa
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dTyr
<220> FEATURE:
<221> NAME/KEY: MISC_FEATURE
<222> LOCATION: (5)..(5)
<223> OTHER INFORMATION: where Xaa is dAla

<400> SEQUENCE: 22

Asp Gly Xaa Tyr Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dTrp
<220> FEATURE:
<221> NAME/KEY: MISC_FEATURE
<222> LOCATION: (5)..(5)
<223> OTHER INFORMATION: where Xaa is dAla

<400> SEQUENCE: 23

Asp Gly Xaa Tyr Xaa
1               5

<210> SEQ ID NO 24
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dHis
<220> FEATURE:
<221> NAME/KEY: MISC_FEATURE
<222> LOCATION: (5)..(5)
<223> OTHER INFORMATION: where Xaa is dAla

<400> SEQUENCE: 24

Asp Gly Xaa Tyr Xaa
1               5
```

```
<210> SEQ ID NO 25
<211> LENGTH: 5
<212> TYPE: PRT
<213> ORGANISM: Artificial Sequence
<220> FEATURE:
<223> OTHER INFORMATION: synthetic peptide

<400> SEQUENCE: 25

Asp Gly Phe Tyr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: synthetic peptide

<400> SEQUENCE: 26

Asp Gly Tyr Tyr Gly
1               5

<210> SEQ ID NO 27
<211> LENGTH: 5
<212> TYPE: PRT
<213> ORGANISM: Artificial Sequence
<220> FEATURE:
<223> OTHER INFORMATION: synthetic peptide

<400> SEQUENCE: 27

Asp Gly Trp Tyr Gly
1               5

<210> SEQ ID NO 28
<211> LENGTH: 5
<212> TYPE: PRT
<213> ORGANISM: Artificial Sequence
<220> FEATURE:
<223> OTHER INFORMATION: synthetic peptide

<400> SEQUENCE: 28

Asp Gly His Tyr Gly
1               5

<210> SEQ ID NO 29
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dPhe

<400> SEQUENCE: 29

Asp Gly Xaa Tyr Gly
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
```

```
<222> LOCATION: (3)..(3)
<223> OTHER INFORMATION: where Xaa is dTyr

<400> SEQUENCE: 30

Asp Gly Xaa Tyr Gly
1               5

<210> SEQ ID NO 31
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dTrp

<400> SEQUENCE: 31

Asp Gly Xaa Tyr Gly
1               5

<210> SEQ ID NO 32
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dHis

<400> SEQUENCE: 32

Asp Gly Xaa Tyr Gly
1               5

<210> SEQ ID NO 33
<211> LENGTH: 5
<212> TYPE: PRT
<213> ORGANISM: Artificial Sequence
<220> FEATURE:
<223> OTHER INFORMATION: synthetic peptide

<400> SEQUENCE: 33

Asp Gly Phe Tyr Pro
1               5

<210> SEQ ID NO 34
<211> LENGTH: 5
<212> TYPE: PRT
<213> ORGANISM: Artificial Sequence
<220> FEATURE:
<223> OTHER INFORMATION: synthetic peptide

<400> SEQUENCE: 34

Asp Gly Tyr Tyr Pro
1               5

<210> SEQ ID NO 35
<211> LENGTH: 5
<212> TYPE: PRT
<213> ORGANISM: Artificial Sequence
<220> FEATURE:
<223> OTHER INFORMATION: synthetic peptide

<400> SEQUENCE: 35

Asp Gly Trp Tyr Pro
```

```
1               5

<210> SEQ ID NO 36
<211> LENGTH: 5
<212> TYPE: PRT
<213> ORGANISM: Artificial Sequence
<220> FEATURE:
<223> OTHER INFORMATION: synthetic peptide

<400> SEQUENCE: 36

Asp Gly His Tyr Pro
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dPhe

<400> SEQUENCE: 37

Asp Gly Xaa Tyr Pro
1               5

<210> SEQ ID NO 38
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dTyr

<400> SEQUENCE: 38

Asp Gly Xaa Tyr Pro
1               5

<210> SEQ ID NO 39
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dTrp

<400> SEQUENCE: 39

Asp Gly Xaa Tyr Pro
1               5

<210> SEQ ID NO 40
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dHis

<400> SEQUENCE: 40
```

Asp Gly Xaa Tyr Pro
1               5

<210> SEQ ID NO 41
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: where Xaa is dPro

<400> SEQUENCE: 41

Asp Gly Phe Tyr Xaa
1               5

<210> SEQ ID NO 42
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: where Xaa is dPro

<400> SEQUENCE: 42

Asp Gly Tyr Tyr Xaa
1               5

<210> SEQ ID NO 43
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: where Xaa is dPro

<400> SEQUENCE: 43

Asp Gly Trp Tyr Xaa
1               5

<210> SEQ ID NO 44
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: where Xaa is dPro

<400> SEQUENCE: 44

Asp Gly His Tyr Xaa
1               5

<210> SEQ ID NO 45
<211> LENGTH: 5
<212> TYPE: PRT
<213> ORGANISM: Artificial Sequence
<220> FEATURE:
<223> OTHER INFORMATION: synthetic peptide

```
<220> FEATURE:
<221> NAME/KEY: MISC_FEATURE
<222> LOCATION: (3)..(3)
<223> OTHER INFORMATION: where Xaa is dPhe
<220> FEATURE:
<221> NAME/KEY: MISC_FEATURE
<222> LOCATION: (5)..(5)
<223> OTHER INFORMATION: where Xaa is dPro

<400> SEQUENCE: 45

Asp Gly Xaa Tyr Xaa
1               5

<210> SEQ ID NO 46
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dTyr
<220> FEATURE:
<221> NAME/KEY: MISC_FEATURE
<222> LOCATION: (5)..(5)
<223> OTHER INFORMATION: where Xaa is dPro

<400> SEQUENCE: 46

Asp Gly Xaa Tyr Xaa
1               5

<210> SEQ ID NO 47
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where X is dTrp
<220> FEATURE:
<221> NAME/KEY: MISC_FEATURE
<222> LOCATION: (5)..(5)
<223> OTHER INFORMATION: where X is dPro

<400> SEQUENCE: 47

Asp Gly Xaa Tyr Xaa
1               5

<210> SEQ ID NO 48
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dHis
<220> FEATURE:
<221> NAME/KEY: MISC_FEATURE
<222> LOCATION: (5)..(5)
<223> OTHER INFORMATION: where Xaa is dPro

<400> SEQUENCE: 48

Asp Gly Xaa Tyr Xaa
1               5

<210> SEQ ID NO 49
```

```
<211> LENGTH: 4
<212> TYPE: PRT
<213> ORGANISM: Artificial Sequence
<220> FEATURE:
<223> OTHER INFORMATION: synthetic peptide

<400> SEQUENCE: 49

Tyr Met Asp Val
1

<210> SEQ ID NO 50
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 50

Xaa Met Asp Val
1

<210> SEQ ID NO 51
<211> LENGTH: 4
<212> TYPE: PRT
<213> ORGANISM: Artificial Sequence
<220> FEATURE:
<223> OTHER INFORMATION: synthetic peptide

<400> SEQUENCE: 51

Phe Met Asp Val
1

<210> SEQ ID NO 52
<211> LENGTH: 4
<212> TYPE: PRT
<213> ORGANISM: Artificial Sequence
<220> FEATURE:
<223> OTHER INFORMATION: Cruse
<220> FEATURE:
<221> NAME/KEY: MISC_FEATURE
<222> LOCATION: (1)..(1)
<223> OTHER INFORMATION: where Xaa is dPhe

<400> SEQUENCE: 52

Xaa Met Asp Val
1

<210> SEQ ID NO 53
<211> LENGTH: 4
<212> TYPE: PRT
<213> ORGANISM: Artificial Sequence
<220> FEATURE:
<223> OTHER INFORMATION: synthetic peptide

<400> SEQUENCE: 53

Tyr Lys Asp Val
1

<210> SEQ ID NO 54
<211> LENGTH: 4
<212> TYPE: PRT
<213> ORGANISM: Artificial Sequence
<220> FEATURE:
<223> OTHER INFORMATION: synthetic peptide
<220> FEATURE:
```

```
<221> NAME/KEY: MISC_FEATURE
<222> LOCATION: (1)..(1)
<223> OTHER INFORMATION: where Xaa is dTyr

<400> SEQUENCE: 54

Xaa Lys Asp Val
1

<210> SEQ ID NO 55
<211> LENGTH: 4
<212> TYPE: PRT
<213> ORGANISM: Artificial Sequence
<220> FEATURE:
<223> OTHER INFORMATION: synthetic peptide

<400> SEQUENCE: 55

Phe Lys Asp Val
1

<210> SEQ ID NO 56
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 56

Xaa Lys Asp Val
1

<210> SEQ ID NO 57
<211> LENGTH: 5
<212> TYPE: PRT
<213> ORGANISM: Artificial Sequence
<220> FEATURE:
<223> OTHER INFORMATION: synthetic peptide

<400> SEQUENCE: 57

Tyr Met Asp Val Lys
1               5

<210> SEQ ID NO 58
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 58

Xaa Met Asp Val Lys
1               5

<210> SEQ ID NO 59
<211> LENGTH: 5
<212> TYPE: PRT
<213> ORGANISM: Artificial Sequence
<220> FEATURE:
<223> OTHER INFORMATION: synthetic peptide

<400> SEQUENCE: 59
```

```
Phe Met Asp Val Lys
1               5

<210> SEQ ID NO 60
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 60

Xaa Met Asp Val Lys
1               5

<210> SEQ ID NO 61
<211> LENGTH: 5
<212> TYPE: PRT
<213> ORGANISM: Artificial Sequence
<220> FEATURE:
<223> OTHER INFORMATION: synthetic peptide

<400> SEQUENCE: 61

Tyr Lys Asp Val Lys
1               5

<210> SEQ ID NO 62
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 62

Xaa Lys Asp Val Lys
1               5

<210> SEQ ID NO 63
<211> LENGTH: 5
<212> TYPE: PRT
<213> ORGANISM: Artificial Sequence
<220> FEATURE:
<223> OTHER INFORMATION: synthetic peptide

<400> SEQUENCE: 63

Phe Lys Asp Val Lys
1               5

<210> SEQ ID NO 64
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 64

Xaa Lys Asp Val Lys
1               5
```

```
<210> SEQ ID NO 65
<211> LENGTH: 5
<212> TYPE: PRT
<213> ORGANISM: Artificial Sequence
<220> FEATURE:
<223> OTHER INFORMATION: synthetic peptide

<400> SEQUENCE: 65

Tyr Met Asp Val Gly
1               5

<210> SEQ ID NO 66
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 66

Xaa Met Asp Val Gly
1               5

<210> SEQ ID NO 67
<211> LENGTH: 5
<212> TYPE: PRT
<213> ORGANISM: Artificial Sequence
<220> FEATURE:
<223> OTHER INFORMATION: synthetic peptide

<400> SEQUENCE: 67

Phe Met Asp Val Gly
1               5

<210> SEQ ID NO 68
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 68

Xaa Met Asp Val Gly
1               5

<210> SEQ ID NO 69
<211> LENGTH: 5
<212> TYPE: PRT
<213> ORGANISM: Artificial Sequence
<220> FEATURE:
<223> OTHER INFORMATION: synthetic peptide

<400> SEQUENCE: 69

Tyr Lys Asp Val Gly
1               5

<210> SEQ ID NO 70
<211> LENGTH: 5
<212> TYPE: PRT
<213> ORGANISM: Artificial Sequence
```

```
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 70

Xaa Lys Asp Val Gly
1               5

<210> SEQ ID NO 71
<211> LENGTH: 5
<212> TYPE: PRT
<213> ORGANISM: Artificial Sequence
<220> FEATURE:
<223> OTHER INFORMATION: synthetic peptide

<400> SEQUENCE: 71

Phe Lys Asp Val Gly
1               5

<210> SEQ ID NO 72
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 72

Xaa Lys Asp Val Gly
1               5

<210> SEQ ID NO 73
<211> LENGTH: 6
<212> TYPE: PRT
<213> ORGANISM: Artificial Sequence
<220> FEATURE:
<223> OTHER INFORMATION: synthetic peptide

<400> SEQUENCE: 73

Tyr Met Asp Val Lys Gly
1               5

<210> SEQ ID NO 74
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 74

Xaa Met Asp Val Lys Gly
1               5

<210> SEQ ID NO 75
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 75

Phe Met Asp Val Lys Gly
1               5

<210> SEQ ID NO 76
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 76

Xaa Met Asp Val Lys Gly
1               5

<210> SEQ ID NO 77
<211> LENGTH: 6
<212> TYPE: PRT
<213> ORGANISM: Artificial Sequence
<220> FEATURE:
<223> OTHER INFORMATION: synthetic peptide

<400> SEQUENCE: 77

Tyr Lys Asp Val Lys Gly
1               5

<210> SEQ ID NO 78
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 78

Xaa Lys Asp Val Lys Gly
1               5

<210> SEQ ID NO 79
<211> LENGTH: 6
<212> TYPE: PRT
<213> ORGANISM: Artificial Sequence
<220> FEATURE:
<223> OTHER INFORMATION: synthetic peptide

<400> SEQUENCE: 79

Phe Lys Asp Val Lys Gly
1               5

<210> SEQ ID NO 80
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 80
```

-continued

```
Xaa Lys Asp Val Lys Gly
1               5

<210> SEQ ID NO 81
<211> LENGTH: 6
<212> TYPE: PRT
<213> ORGANISM: Artificial Sequence
<220> FEATURE:
<223> OTHER INFORMATION: synthetic peptide

<400> SEQUENCE: 81

Tyr Met Asp Val Gly Gly
1               5

<210> SEQ ID NO 82
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 82

Xaa Met Asp Val Gly Gly
1               5

<210> SEQ ID NO 83
<211> LENGTH: 6
<212> TYPE: PRT
<213> ORGANISM: Artificial Sequence
<220> FEATURE:
<223> OTHER INFORMATION: synthetic peptide

<400> SEQUENCE: 83

Phe Met Asp Val Gly Gly
1               5

<210> SEQ ID NO 84
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 84

Xaa Met Asp Val Gly Gly
1               5

<210> SEQ ID NO 85
<211> LENGTH: 6
<212> TYPE: PRT
<213> ORGANISM: Artificial Sequence
<220> FEATURE:
<223> OTHER INFORMATION: synthetic peptide

<400> SEQUENCE: 85

Tyr Lys Asp Val Gly Gly
1               5

<210> SEQ ID NO 86
```

```
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where as Xaa is dTyr

<400> SEQUENCE: 86

Xaa Lys Asp Val Gly Gly
1               5

<210> SEQ ID NO 87
<211> LENGTH: 6
<212> TYPE: PRT
<213> ORGANISM: Artificial Sequence
<220> FEATURE:
<223> OTHER INFORMATION: synthetic peptide

<400> SEQUENCE: 87

Phe Lys Asp Val Gly Gly
1               5

<210> SEQ ID NO 88
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 88

Xaa Lys Asp Val Gly Gly
1               5

<210> SEQ ID NO 89
<211> LENGTH: 7
<212> TYPE: PRT
<213> ORGANISM: Artificial Sequence
<220> FEATURE:
<223> OTHER INFORMATION: synthetic peptide

<400> SEQUENCE: 89

Tyr Met Asp Val Lys Gly Gly
1               5

<210> SEQ ID NO 90
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 90

Xaa Met Asp Val Lys Gly Gly
1               5

<210> SEQ ID NO 91
<211> LENGTH: 7
<212> TYPE: PRT
```

```
<213> ORGANISM: Artificial Sequence
<220> FEATURE:
<223> OTHER INFORMATION: synthetic peptide

<400> SEQUENCE: 91

Phe Met Asp Val Lys Gly Gly
1               5

<210> SEQ ID NO 92
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 92

Xaa Met Asp Val Lys Gly Gly
1               5

<210> SEQ ID NO 93
<211> LENGTH: 7
<212> TYPE: PRT
<213> ORGANISM: Artificial Sequence
<220> FEATURE:
<223> OTHER INFORMATION: synthetic peptide

<400> SEQUENCE: 93

Tyr Lys Asp Val Lys Gly Gly
1               5

<210> SEQ ID NO 94
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 94

Xaa Lys Asp Val Lys Gly Gly
1               5

<210> SEQ ID NO 95
<211> LENGTH: 7
<212> TYPE: PRT
<213> ORGANISM: Artificial Sequence
<220> FEATURE:
<223> OTHER INFORMATION: synthetic peptide

<400> SEQUENCE: 95

Phe Lys Asp Val Lys Gly Gly
1               5

<210> SEQ ID NO 96
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
```

<223> OTHER INFORMATION: where Xaa is dPhe

<400> SEQUENCE: 96

Xaa Lys Asp Val Lys Gly Gly
1               5

<210> SEQ ID NO 97
<211> LENGTH: 7
<212> TYPE: PRT
<213> ORGANISM: Artificial Sequence
<220> FEATURE:
<223> OTHER INFORMATION: synthetic peptide

<400> SEQUENCE: 97

Tyr Met Asp Val Gly Gly Ser
1               5

<210> SEQ ID NO 98
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 98

Xaa Met Asp Val Gly Gly Ser
1               5

<210> SEQ ID NO 99
<211> LENGTH: 7
<212> TYPE: PRT
<213> ORGANISM: Artificial Sequence
<220> FEATURE:
<223> OTHER INFORMATION: synthetic peptide

<400> SEQUENCE: 99

Phe Met Asp Val Gly Gly Ser
1               5

<210> SEQ ID NO 100
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 100

Xaa Met Asp Val Gly Gly Ser
1               5

<210> SEQ ID NO 101
<211> LENGTH: 7
<212> TYPE: PRT
<213> ORGANISM: Artificial Sequence
<220> FEATURE:
<223> OTHER INFORMATION: synthetic peptide

<400> SEQUENCE: 101

Tyr Lys Asp Val Gly Gly Ser
1               5

```
<210> SEQ ID NO 102
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 102

Xaa Lys Asp Val Gly Gly Ser
1               5

<210> SEQ ID NO 103
<211> LENGTH: 7
<212> TYPE: PRT
<213> ORGANISM: Artificial Sequence
<220> FEATURE:
<223> OTHER INFORMATION: synthetic peptide

<400> SEQUENCE: 103

Phe Lys Asp Val Gly Gly Ser
1               5

<210> SEQ ID NO 104
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 104

Xaa Lys Asp Val Gly Gly Ser
1               5

<210> SEQ ID NO 105
<211> LENGTH: 8
<212> TYPE: PRT
<213> ORGANISM: Artificial Sequence
<220> FEATURE:
<223> OTHER INFORMATION: synthetic peptide

<400> SEQUENCE: 105

Tyr Met Asp Val Lys Gly Gly Ser
1               5

<210> SEQ ID NO 106
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 106

Xaa Met Asp Val Lys Gly Gly Ser
1               5
```

```
<210> SEQ ID NO 107
<211> LENGTH: 8
<212> TYPE: PRT
<213> ORGANISM: Artificial Sequence
<220> FEATURE:
<223> OTHER INFORMATION: synthetic peptide

<400> SEQUENCE: 107

Phe Met Asp Val Lys Gly Gly Ser
1               5

<210> SEQ ID NO 108
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe

<400> SEQUENCE: 108

Xaa Met Asp Val Lys Gly Gly Ser
1               5

<210> SEQ ID NO 109
<211> LENGTH: 8
<212> TYPE: PRT
<213> ORGANISM: Artificial Sequence
<220> FEATURE:
<223> OTHER INFORMATION: synthetic peptide

<400> SEQUENCE: 109

Tyr Lys Asp Val Lys Gly Gly Ser
1               5

<210> SEQ ID NO 110
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dTyr

<400> SEQUENCE: 110

Xaa Lys Asp Val Lys Gly Gly Ser
1               5

<210> SEQ ID NO 111
<211> LENGTH: 8
<212> TYPE: PRT
<213> ORGANISM: Artificial Sequence
<220> FEATURE:
<223> OTHER INFORMATION: synthetic peptide

<400> SEQUENCE: 111

Phe Lys Asp Val Lys Gly Gly Ser
1               5

<210> SEQ ID NO 112
<211> LENGTH: 8
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MISC_FEATURE
<222> LOCATION: (1)..(1)
<223> OTHER INFORMATION: where Xaa is dPhe

<400> SEQUENCE: 112

Xaa Lys Asp Val Lys Gly Gly Ser
1               5

<210> SEQ ID NO 113
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: where the carboxy group on the last amino acid
      may be replaced by another amino group

<400> SEQUENCE: 113

Tyr Cys Asp Gly Phe Tyr Ala Cys Tyr Met Asp Val
1               5                   10

<210> SEQ ID NO 114
<211> LENGTH: 12
<212> TYPE: PRT
<213> ORGANISM: Artificial Sequence
<220> FEATURE:
<223> OTHER INFORMATION: synthetic peptide

<400> SEQUENCE: 114

Tyr Cys Asp Gly Phe Tyr Ala Cys Tyr Met Asp Val
1               5                   10

<210> SEQ ID NO 115
<211> LENGTH: 13
<212> TYPE: PRT
<213> ORGANISM: Artificial Sequence
<220> FEATURE:
<223> OTHER INFORMATION: synthetic peptide

<400> SEQUENCE: 115

Gly Tyr Cys Asp Gly Phe Tyr Ala Cys Tyr Met Asp Val
1               5                   10

<210> SEQ ID NO 116
<211> LENGTH: 14
<212> TYPE: PRT
<213> ORGANISM: Artificial Sequence
<220> FEATURE:
<223> OTHER INFORMATION: synthetic peptide

<400> SEQUENCE: 116

Gly Gly Tyr Cys Asp Gly Phe Tyr Ala Cys Tyr Met Asp Val
1               5                   10

<210> SEQ ID NO 117
<211> LENGTH: 15
<212> TYPE: PRT
<213> ORGANISM: Artificial Sequence
<220> FEATURE:
<223> OTHER INFORMATION: synthetic peptide

<400> SEQUENCE: 117

Gly Gly Gly Tyr Cys Asp Gly Phe Tyr Ala Cys Tyr Met Asp Val
1               5                   10                  15
```

<210> SEQ ID NO 118
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: where the carboxy group on the last amino acid
      may be replaced by another amino group
<220> FEATURE:
<221> NAME/KEY: MISC_FEATURE
<222> LOCATION: (1)..(1)
<223> OTHER INFORMATION: where Xaa is dPhe
<220> FEATURE:
<221> NAME/KEY: MISC_FEATURE
<222> LOCATION: (9)..(9)
<223> OTHER INFORMATION: where Xaa is dTyr

<400> SEQUENCE: 118

Xaa Cys Asp Gly Phe Tyr Ala Cys Xaa Met Asp Val
1               5                   10

<210> SEQ ID NO 119
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe
<220> FEATURE:
<221> NAME/KEY: MISC_FEATURE
<222> LOCATION: (9)..(9)
<223> OTHER INFORMATION: where Xaa is dTyr

<400> SEQUENCE: 119

Xaa Cys Asp Gly Phe Tyr Ala Cys Xaa Met Asp Val
1               5                   10

<210> SEQ ID NO 120
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: where Xaa is dPhe
<220> FEATURE:
<221> NAME/KEY: MISC_FEATURE
<222> LOCATION: (10)..(10)
<223> OTHER INFORMATION: where Xaa is dTyr

<400> SEQUENCE: 120

Gly Xaa Cys Asp Gly Phe Tyr Ala Cys Xaa Met Asp Val
1               5                   10

<210> SEQ ID NO 121
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)

<223> OTHER INFORMATION: where Xaa is dPhe
<220> FEATURE:
<221> NAME/KEY: MISC_FEATURE
<222> LOCATION: (11)..(11)
<223> OTHER INFORMATION: where Xaa is dTyr

<400> SEQUENCE: 121

Gly Gly Xaa Cys Asp Gly Phe Tyr Ala Cys Xaa Met Asp Val
1               5                   10

<210> SEQ ID NO 122
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: where Xaa is dPhe
<220> FEATURE:
<221> NAME/KEY: MISC_FEATURE
<222> LOCATION: (12)..(12)
<223> OTHER INFORMATION: where Xaa is dTyr

<400> SEQUENCE: 122

Gly Gly Gly Xaa Cys Asp Gly Phe Tyr Ala Cys Xaa Met Asp Val
1               5                   10                  15

<210> SEQ ID NO 123
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: where the carboxy group on the last amino acid
      may be replaced by another amino group

<400> SEQUENCE: 123

Phe Cys Asp Gly Phe Tyr Ala Cys Tyr Met Asp Val Lys
1               5                   10

<210> SEQ ID NO 124
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: where Xaa is dPhe
<220> FEATURE:
<221> NAME/KEY: MISC_FEATURE
<222> LOCATION: (9)..(9)
<223> OTHER INFORMATION: where Xaa is dTyr

<400> SEQUENCE: 124

Xaa Cys Asp Gly Phe Tyr Ala Cys Xaa Met Asp Val Lys
1               5                   10

<210> SEQ ID NO 125
<211> LENGTH: 14
<212> TYPE: PRT
<213> ORGANISM: Artificial Sequence
<220> FEATURE:
<223> OTHER INFORMATION: synthetic peptide
<220> FEATURE:

-continued

```
<221> NAME/KEY: MISC_FEATURE
<222> LOCATION: (2)..(2)
<223> OTHER INFORMATION: where Xaa is dPhe
<220> FEATURE:
<221> NAME/KEY: MISC_FEATURE
<222> LOCATION: (10)..(10)
<223> OTHER INFORMATION: where Xaa is dTyr

<400> SEQUENCE: 125

Gly Xaa Cys Asp Gly Phe Tyr Ala Cys Xaa Met Asp Val Lys
1               5                   10

<210> SEQ ID NO 126
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: where Xaa is dPhe
<220> FEATURE:
<221> NAME/KEY: MISC_FEATURE
<222> LOCATION: (11)..(11)
<223> OTHER INFORMATION: where Xaa is dTyr

<400> SEQUENCE: 126

Gly Gly Xaa Cys Asp Gly Phe Tyr Ala Cys Xaa Met Asp Val Lys
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: where Xaa is dPhe
<220> FEATURE:
<221> NAME/KEY: MISC_FEATURE
<222> LOCATION: (12)..(12)
<223> OTHER INFORMATION: where Xaa is dTyr

<400> SEQUENCE: 127

Gly Gly Gly Xaa Cys Asp Gly Phe Tyr Ala Cys Xaa Met Asp Val Lys
1               5                   10                  15

<210> SEQ ID NO 128
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: where the carboxy group on the last amino acid
      may be replaced by another amino group

<400> SEQUENCE: 128

Phe Cys Asp Gly Phe Tyr Ala Cys Tyr Lys Asp Val
1               5                   10

<210> SEQ ID NO 129
<211> LENGTH: 12
<212> TYPE: PRT
<213> ORGANISM: Artificial Sequence
<220> FEATURE:
```

<223> OTHER INFORMATION: synthetic peptide

<400> SEQUENCE: 129

Phe Cys Asp Gly Phe Tyr Ala Cys Tyr Lys Asp Val
1               5                   10

<210> SEQ ID NO 130
<211> LENGTH: 13
<212> TYPE: PRT
<213> ORGANISM: Artificial Sequence
<220> FEATURE:
<223> OTHER INFORMATION: synthetic peptide

<400> SEQUENCE: 130

Gly Phe Cys Asp Gly Phe Tyr Ala Cys Tyr Met Asp Val
1               5                   10

<210> SEQ ID NO 131
<211> LENGTH: 14
<212> TYPE: PRT
<213> ORGANISM: Artificial Sequence
<220> FEATURE:
<223> OTHER INFORMATION: synthetic peptide

<400> SEQUENCE: 131

Gly Gly Phe Cys Asp Gly Phe Tyr Ala Cys Tyr Lys Asp Val
1               5                   10

<210> SEQ ID NO 132
<211> LENGTH: 15
<212> TYPE: PRT
<213> ORGANISM: Artificial Sequence
<220> FEATURE:
<223> OTHER INFORMATION: synthetic peptide

<400> SEQUENCE: 132

Gly Gly Gly Phe Cys Asp Gly Phe Tyr Ala Cys Tyr Lys Asp Val
1               5                   10                  15

<210> SEQ ID NO 133
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: where the carboxy group on the last amino acid
      may be replaced by another amino group

<400> SEQUENCE: 133

Gly Phe Cys Asp Gly Phe Tyr Ala Cys Tyr Met Asp Val
1               5                   10

<210> SEQ ID NO 134
<211> LENGTH: 13
<212> TYPE: PRT
<213> ORGANISM: Artificial Sequence
<220> FEATURE:
<223> OTHER INFORMATION: synthetic peptide

<400> SEQUENCE: 134

Gly Phe Cys Asp Gly Phe Tyr Ala Cys Tyr Met Asp Val
1               5                   10

<210> SEQ ID NO 135

```
<211> LENGTH: 14
<212> TYPE: PRT
<213> ORGANISM: Artificial Sequence
<220> FEATURE:
<223> OTHER INFORMATION: synthetic peptide

<400> SEQUENCE: 135

Gly Phe Cys Asp Gly Phe Tyr Ala Cys Tyr Met Asp Val Gly
1               5                   10

<210> SEQ ID NO 136
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: where Xaa is dTyr

<400> SEQUENCE: 136

Gly Phe Cys Asp Gly Phe Tyr Ala Cys Xaa Met Asp Val Gly Gly
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: where Xaa is dTyr

<400> SEQUENCE: 137

Gly Phe Cys Asp Gly Phe Tyr Ala Cys Xaa Met Asp Val Gly Gly Gly
1               5                   10                  15

<210> SEQ ID NO 138
<211> LENGTH: 6
<212> TYPE: PRT
<213> ORGANISM: Artificial Sequence
<220> FEATURE:
<223> OTHER INFORMATION: synthetic peptide

<400> SEQUENCE: 138

Gly Asp Gly Phe Tyr Ala
1               5

<210> SEQ ID NO 139
<211> LENGTH: 6
<212> TYPE: PRT
<213> ORGANISM: Artificial Sequence
<220> FEATURE:
<223> OTHER INFORMATION: synthetic peptide

<400> SEQUENCE: 139

Gly Asp Gly Phe Tyr Ala
1               5

<210> SEQ ID NO 140
<211> LENGTH: 5
<212> TYPE: PRT
<213> ORGANISM: Artificial Sequence
<220> FEATURE:
<223> OTHER INFORMATION: synthetic peptide
```

```
<400> SEQUENCE: 140

Asp Pro Phe Tyr Ala
1               5

<210> SEQ ID NO 141
<211> LENGTH: 6
<212> TYPE: PRT
<213> ORGANISM: Artificial Sequence
<220> FEATURE:
<223> OTHER INFORMATION: synthetic peptide

<400> SEQUENCE: 141

Pro Asp Gly Phe Tyr Ala
1               5

<210> SEQ ID NO 142
<211> LENGTH: 6
<212> TYPE: PRT
<213> ORGANISM: Artificial Sequence
<220> FEATURE:
<223> OTHER INFORMATION: synthetic peptide

<400> SEQUENCE: 142

Asp Pro Pro Phe Tyr Ala
1               5

<210> SEQ ID NO 143
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: where the carboxy group on the last amino acid
      may be replaced by another amino group

<400> SEQUENCE: 143

Phe Cys Gly Asp Gly Phe Tyr Ala Cys Tyr Met Asp Val
1               5                   10

<210> SEQ ID NO 144
<211> LENGTH: 13
<212> TYPE: PRT
<213> ORGANISM: Artificial Sequence
<220> FEATURE:
<223> OTHER INFORMATION: synthetic peptide

<400> SEQUENCE: 144

Phe Cys Gly Asp Gly Phe Tyr Ala Cys Tyr Met Asp Val
1               5                   10

<210> SEQ ID NO 145
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: where the carboxy group on the last amino acid
      may be replaced by another amino group

<400> SEQUENCE: 145

Phe Cys Asp Gly Phe Tyr Ala Cys Tyr Met Asp Val
1               5                   10
```

-continued

```
<210> SEQ ID NO 146
<211> LENGTH: 12
<212> TYPE: PRT
<213> ORGANISM: Artificial Sequence
<220> FEATURE:
<223> OTHER INFORMATION: synthetic peptide

<400> SEQUENCE: 146

Phe Cys Asp Gly Phe Tyr Ala Cys Tyr Met Asp Val
1               5                   10

<210> SEQ ID NO 147
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: where the carboxy group on the last amino acid
      may be replaced by another amino group

<400> SEQUENCE: 147

Phe Cys Asp Pro Phe Tyr Ala Cys Tyr Met Asp Val
1               5                   10

<210> SEQ ID NO 148
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: where the carboxy group o nthe last amino acid
      may be replaced by another amino group

<400> SEQUENCE: 148

Phe Cys Pro Asp Gly Phe Tyr Ala Cys Tyr Met Asp Val
1               5                   10

<210> SEQ ID NO 149
<211> LENGTH: 13
<212> TYPE: PRT
<213> ORGANISM: Artificial Sequence
<220> FEATURE:
<223> OTHER INFORMATION: synthetic peptide

<400> SEQUENCE: 149

Phe Cys Pro Asp Gly Phe Tyr Ala Cys Tyr Met Asp Val
1               5                   10

<210> SEQ ID NO 150
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: where the carboxy group on the last amino acid
      may be replaced by another amino group

<400> SEQUENCE: 150

Phe Cys Asp Pro Pro Phe Tyr Ala Cys Tyr Met Asp Val
```

```
<210> SEQ ID NO 151
<211> LENGTH: 13
<212> TYPE: PRT
<213> ORGANISM: Artificial Sequence
<220> FEATURE:
<223> OTHER INFORMATION: synthetic peptide

<400> SEQUENCE: 151

Phe Cys Asp Pro Pro Phe Tyr Ala Cys Tyr Met Asp Val
1               5                   10

<210> SEQ ID NO 152
<211> LENGTH: 12
<212> TYPE: PRT
<213> ORGANISM: Artificial Sequence
<220> FEATURE:
<223> OTHER INFORMATION: synthetic peptide

<400> SEQUENCE: 152

Phe Cys Asp Pro Phe Tyr Ala Cys Tyr Met Asp Val
1               5                   10
```

COMPOUNDS THAT BIND TO P185 AND METHODS OF USING THE SAME

This application claims priority under 35 U.S.C. §119(e) to U.S. Provisional Application Ser. No. 60/331,935, filed Nov. 21, 2001, which is incorporated herein by reference in its entirety.

FIELD OF THE INVENTION

The invention relates to compounds useful for and methods of treating individuals suspected of suffering from tumors and preventing tumors in individuals suspected of being susceptible to the development of tumors and for detecting and imaging tumors.

BACKGROUND OF THE INVENTION

Significant amounts of time and money have been spent to better understand cancer and searching for ways to prevent and cure cancer. The results of these research efforts have provided a greater understanding of the biological and biochemical events that participate in the formation of tumors.

Malignant cells display a variety of characteristics that distinguish them from normal cells. Recent studies in the molecular genetics of cancer indicate that certain genes known as oncogenes may play a role in the transformation of some cells from their normal condition to a cancerous condition. Proto-oncogenes, genes closely related to these genes, are found in somatic cells of all eukaryotic species examined and have been highly conserved in evolution; it is thought that proto-oncogenes normally play critical roles in cellular growth and development. Oncogene amplification and chromosomal rearrangements involving oncogenes have been detected in a large number of tumors. Furthermore some tumors have been shown to contain activated oncogenes-which, in DNA transfection assays, are capable of conferring neoplastic properties upon non-neoplastic rodent fibroblast cell lines. Collectively these studies suggest that alterations in proto-oncogene structure and function play a critical role in the development of neoplasia.

Although most oncogene-encoded proteins reside in the nucleus or the cytoplasm, some oncogenes encode proteins that are present as antigenic sites on the cell surface. For example, the erbB-1, erbB-2, erbB-3, erbB-4, fms and ros oncogene products are transmembrane glycoproteins that possess extracellular domains. The sis oncogene product may also exist in a membrane associated form on the surface of transformed cells.

Another oncogene which encodes a protein that exposes antigenic sites on the surface of transformed cells has been identified by transfection of DNA from ethyl nitrosourea-induced rat neuroblastomas into NIH3T3 cells. This oncogene has been termed neu. The homologous human gene is called erbB-2. The erbB-2 gene has been found to be amplified or overexpressed in some human tumors, particularly those of the breast, suggesting that this gene may play an imported role in the etiology of human cancer.

The protein encoded by the erbB-2 oncogene is a 185 kDa transmembrane glycoprotein with tyrosine kinase activity, generally known by the name p185. The erbB-2 gene is closely related to the epidermal growth factor (EGF) receptor gene in structure.

The erbB-2 oncogene and p185 has also been found active in human adenocarcinomas including breast, lung, salivary gland and kidney adenocarcinomas, as well as prostate neuroblastoma. In human primary breast cancers, amplification of the erbB-2 oncogene was found in about 30% of all malignant tumors examined. Increased stage of malignancy, characterized by large tumor size and increased number of positive lymph nodes as well as reduced survival time and decreased time to relapse, was directly correlated with an increased level of amplification of the erbB-2 gene. The erbB-2 protooncogene is expressed at low levels in normal human tissues. Further, erbB-2 has been associated with 100% of the ductal carcinomas studied in situ, Lodato, R. F., et al. (1990) *Modern Pathol.* 3(4):449.

Current treatments for individuals suffering from carcinomas expressing amplified levels of erbB-2 include surgery, radiation therapy, chemotherapy, immunotherapy and, usually, combinations of two or more of such therapies. Despite advances made in these fields, the mortality rate among individuals suffering from cancer remains unacceptable high. Complete tumor eradication and total remission is not always the outcome.

There remains a need for additional modalities in the anti-tumor approaches and for additional methods of reducing and/or eliminating tumors in individuals. There is a need for anti-tumor agents which can be administered as therapeutics to individuals suffering form tumors, particularly tumors with amplified levels of p185.

While changes in diet and behavior can reduce the likelihood of developing cancer, it has been found that some individuals have a higher risk of developing cancer than others. Further, those individuals who have already developed cancer and who have been effectively treated face a risk of relapse and recurrence.

Advancements in the understanding of genetics and developments in technology as well as epidemiology allow for the determination of probability and risk assessment an individual has for developing cancer. Using family health histories and/or genetic screening, it is possible to estimate the probability that a particular individual has for developing certain types of cancer. Those individuals that have been identified as being predisposed to developing a particular form of cancer can take only limited prophylactic steps towards reducing the risk of cancer. There is no currently available method or composition which can chemically intervene with the development of cancer and reduce the probability a high risk individual will develop cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

There is a need for improved preventative agents for individuals with a high risk to develop cancer, and for individuals who have had cancer enter remission or be removed (e.g., resected). In cases where the type of cancer the individual is at risk to develop is known, such as tumors associated with erbB-2, there is a need for specific agents which can be administered to reduce the probability that a predisposed individual will develop cancer or that a patient in remission will suffer a relapse.

There is a need for therapeutic compositions useful to treat individuals identified as having p185-associated tumors. There is also a need to develop prophylactic com-

SUMMARY OF THE INVENTION

The present invention relates to peptides having the Formula I or Formula II:

wherein:
- $R_1$, is O-benzyloxy or 1–4 amino acid residues including at least one of tyrosine or phenylalanine;
- $R_2$ is a linking moiety which bonds with $R_1$, $R_3$ and $R_4$ such that a portion of said peptide is cyclicized;
- $R_3$ is 5 amino acids;
- $R_4$ is a linking moiety which bonds with $R_3$, $R_5$ and $R_2$ such that a portion of said peptide is cyclicized;
- $R_5$ is 1–13 amino acid residues and at least one of which is tyrosine or phenylalanine;

wherein: $R_1$, $R_2$, $R_3$, $R_4$, and $R_5$ taken together, are 20 amino acids or less; and $R_3$ is has the formula:

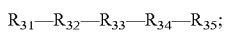

wherein:
- $R_{31}$ is aspartic acid;
- $R_{32}$ is glycine;
- $R_{33}$ is phenylalanine, tyrosine, tryptophan, histidine, D-phenylalanine, D-tyrosine, D-tryptophan, or D-histidine;
- $R_{34}$ is tyrosine; and
- $R_{35}$ is alanine, glycine, proline, D-alanine, D-glycine, or D-proline; and the carboxy terminus of $R_5$ is either amidated or hydroxylated.

wherein
- $R_6$ is 1–4 amino acid residues including at least one of tyrosine or phenylalanine;
- $R_7$ is cysteine;
- $R_8$ is 5–7 amino acids;
- $R_9$ is cysteine;
- $R_{10}$ is 1–13 amino acid residues and at least one of which is tyrosine or phenylalanine;

wherein: $R_6$, $R_7$, $R_8$, $R_9$, and $R_{10}$ taken together, are 20 amino acids or less; and $R_8$ has the formula

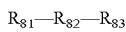

wherein
- $R_{81}$ is glycine-aspartic acid, proline-aspartic acid, or aspartic acid;
- $R_{82}$ is glycine, proline or proline-proline; and
- $R_{83}$ is phenylalanine-tyrosine-alanine;

and the carboxy terminus of $R_{10}$ is either amidated or hydroxylated.

The present invention relates to pharmaceutical compositions which comprise a peptide of Formula I or Formula II in combination with a pharmaceutically acceptable carrier or diluent.

The present invention relates to methods of preventing transformation of a cell which overexposes p185 but is not fully transformed into a transformed tumor cell in an individual at risk of developing a tumor or having tumor cells which have p185 on their surfaces. The method comprises the steps of: identifying such an individual; and administering to the individual peptide of Formula II.

The present invention relates to methods of treating an individual who has cancer characterized by tumor cells that have a p185 on their cell surfaces. The methods comprise the steps of identifying such an individual; and administering to the individual, a therapeutically effective amount of a peptide of Formula I or Formula II.

The present invention relates to conjugated compositions that comprise a peptide linked to a detectable agent and/or a cytotoxic agent, wherein the peptide has either Formula I or Formula II.

The present invention relates to methods of detecting a tumor that has p185 on tumor cell surfaces. The methods comprise the step of administering, to an individual suspected of having such a tumor or being susceptible to such a tumor, a conjugated composition described above which comprises a peptide of Formula I or Formula II linked to a detectable agent and detecting the presence of localized conjugated composition within the body of the individual.

The present invention relates to pharmaceutical compositions which comprise a conjugated compositions described above which comprises a peptide of Formula I or Formula II linked to a detectable agent and/or a cytotoxic agent in combination with a pharmaceutically acceptable carrier or diluent.

The present invention relates to methods of treating an individual who has cancer characterized by tumor cells that have a p185 on their cell surfaces. The methods comprise the steps of identifying such an individual; and administering to the individual, a therapeutically effective amount of a conjugated composition described above which comprises a peptide of Formula I or Formula II linked to a cytotoxic agent.

The present invention relates to co-administration of pharmaceutical compositions which comprise a peptide of Formula I or Formula II with with other treatments for cancer characterized by tumor cells that have a p185 on their cell surfaces, such as Herceptin or tamoxifen.

BRIEF DESCRIPTION OF THE FIGURES

The patent or application file contains at least one drawing executed in color. Copies of this patent or patent application publication with color drawing(s) will be provided by the Office upon request and payment of the necessary fee.

Inset shows correlation between the initial rate of rhumAb 4D5 binding to HER2 and concentration of preinjected AHNP.

Figure 3A:
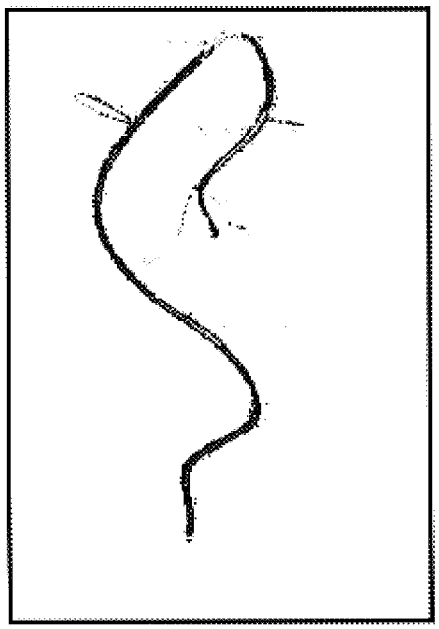
Figure 3B:
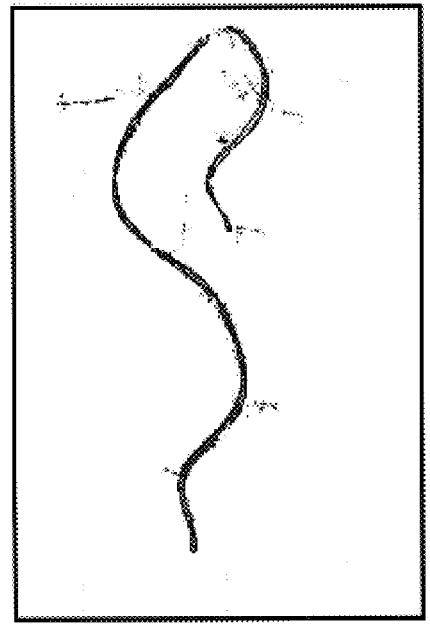
Figure 3C:
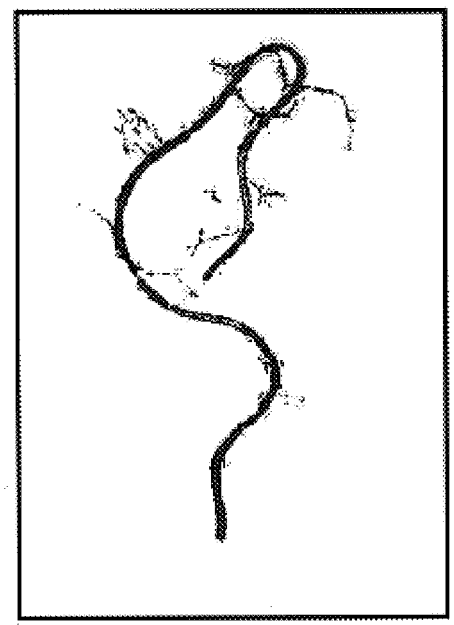

FIGS. 3A, 3B and 3C. Molecular models of AHNP analogues. AHNP (A), 6 (B), and 8 (C). Cys residues forming the disulfide bond are shown in yellow. The Met residue in the tail region of AHNP (A) and the Lys residue replacing Met in 6 (b) are shown in red.

Figure 4A:
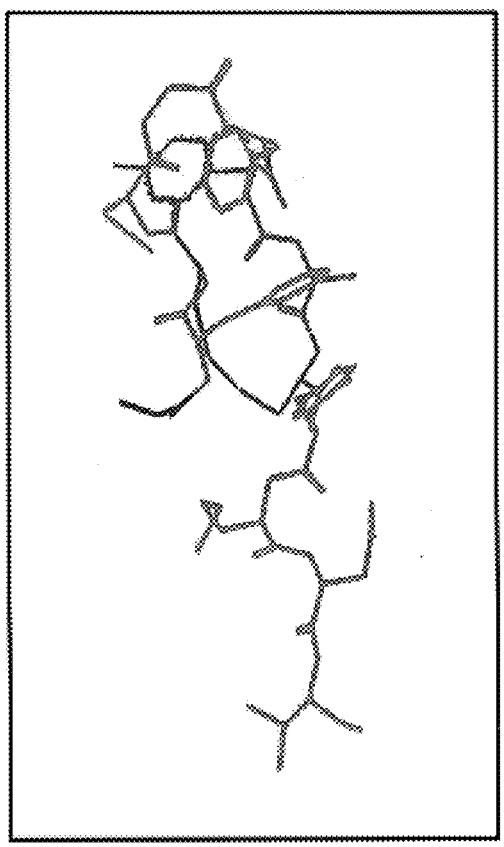
Figure 4B:
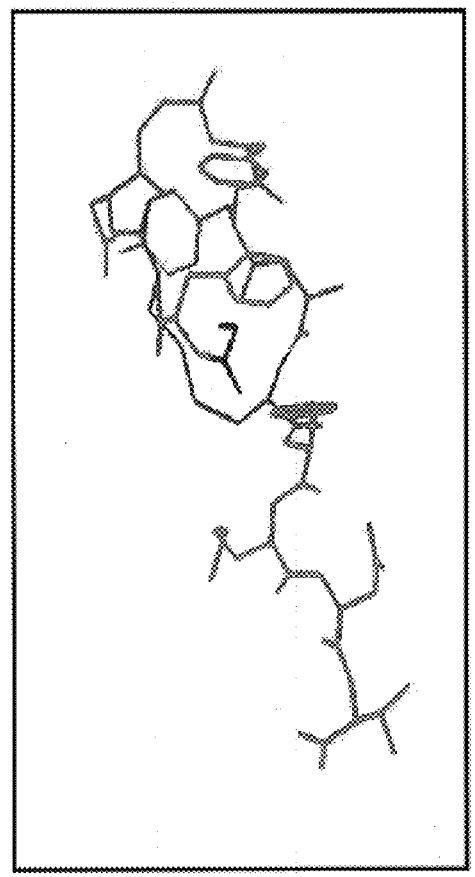

FIGS. 4A and 4B. Low-energy conformers of 7. Molecular models of two low-energy conformers of 7 with the solvent-exposed (A) and buried (B) orientation of the N-terminal Gly. The Gly residue is colored red.

Figure 5:
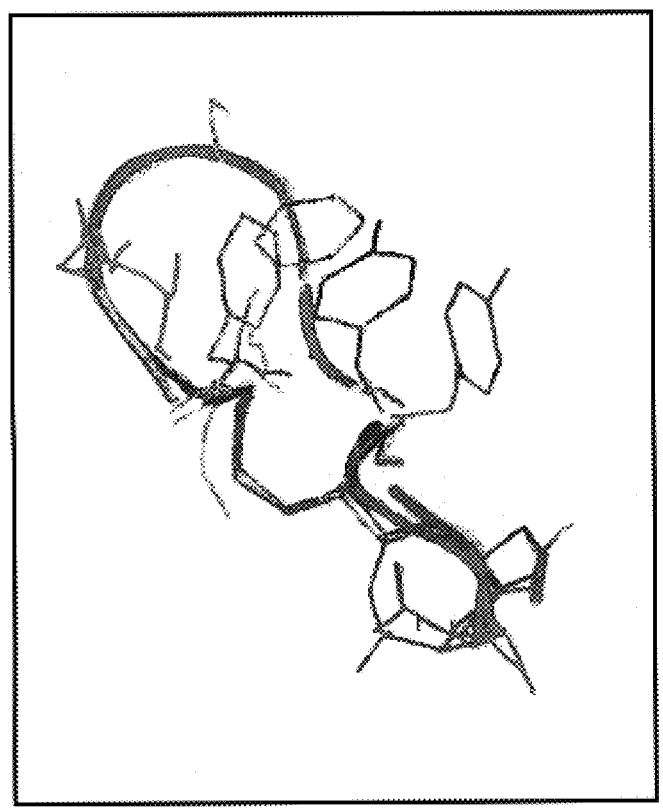

FIG. 5. Molecular model of 4 superimposed with AHNP. Aromatic side chains at both ends of the disulfide bond are colored red for AHNP and white for 4.

FIGS. 6A and 6B. Structure-function analysis of AHNP analogues. Plots show correlation between peptides' activities in MTT assays and (A) their receptor-binding affinities, or (B) dissociation rate constants obtained in Biacore studies.

Figure 7:
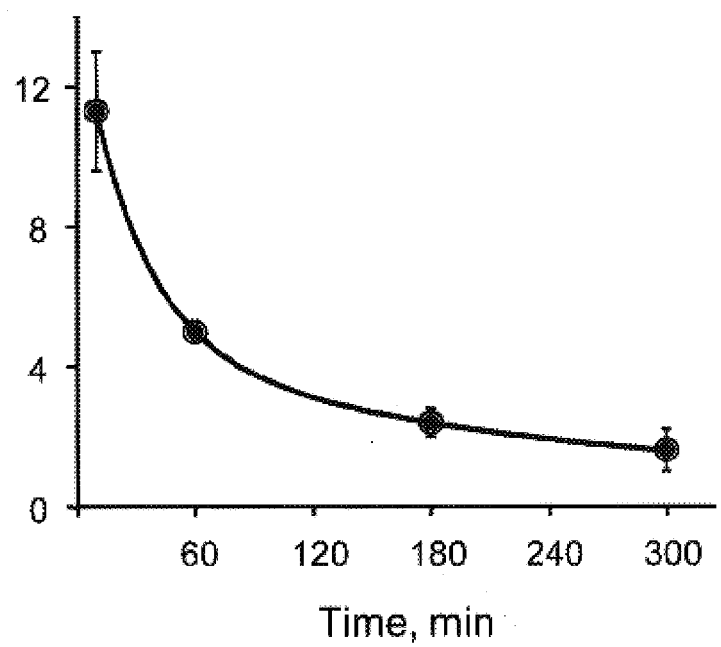

FIG. 7. Graph representing blood clearance of $^{99m}$Tc-labeled AHNP in nude mice.

Figure 8A:
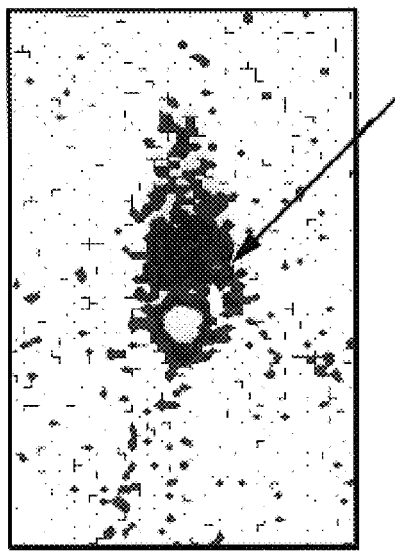
Figure 8B:
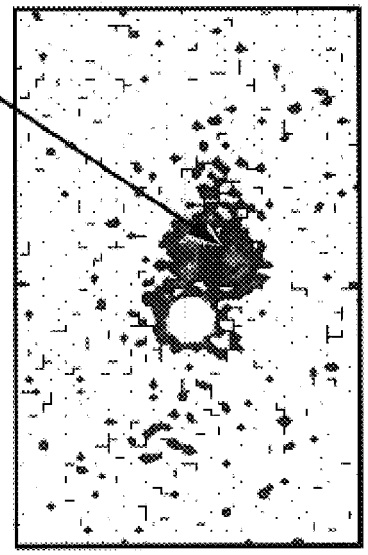

FIGS. 8A and 8B. Radioactive imaging of $^{99m}$Tc-labeled AHNP in xenografted tumor tissue compared with normal tissue after 30 min (FIG. 8A) and 90 min. (FIG. 8B).

Figure 9:
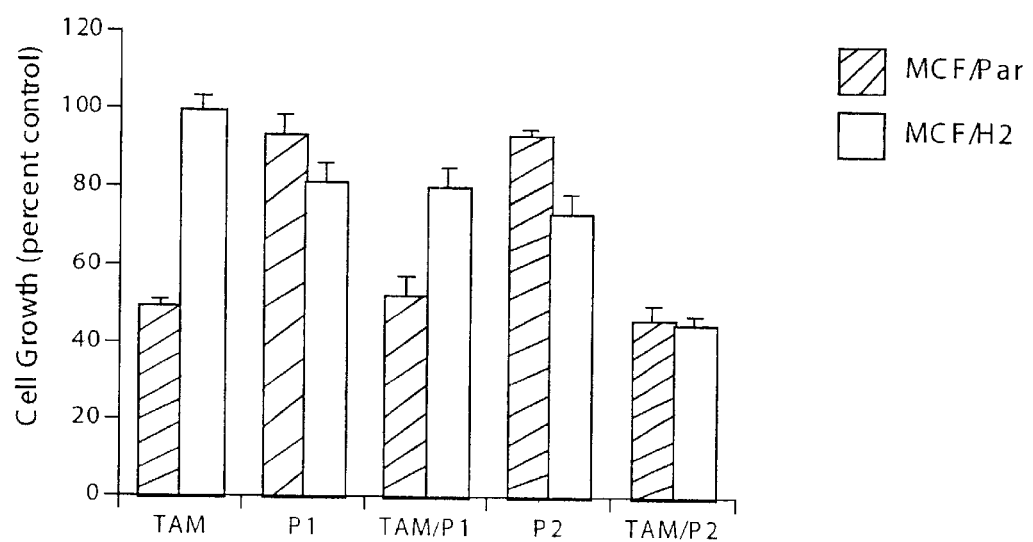

FIG. 9. Graph representing the enhanced growth inhibition of HER-2 overexpressing cells using an AHNP analogue in combination with tamoxifen.

DETAILED DESCRIPTION

Definitions

As used herein, the terms "neu-associated cancer", "erbB-2-associated cancer", "neu-associated tumors", "erbB-2-associated tumors", "p185-mediated tumors" and "p185-associated tumors" are meant to refer to tumor cells and neoplasms which express the erbB-2 gene to produce p185. Examples of erbB-2-associated cancer include many human adenocarcinomas. Breast, ovary, lung, pancreas, salivary gland and kidney adenocarcinomas and prostate, and some neuroblastoma have been found to be erbB-2-associated cancers.

When a therapeutically effective amount of a compound of the invention is administered to an individual who has erbB-2-associated cancer, the effect is that the proliferation rate of tumor cells is slowed down or eliminated. As used herein, the term "compound" is meant to refer to a peptide of Formula I or Formula II, a peptide mimetic or a conjugated compound comprising a peptide of Formula I or Formula II which is useful in the method of detecting, imaging, treating or preventing p185-mediated tumors.

As used herein, the term "therapeutically effective amount" is meant to refer to an amount of a compound which produces a medicinal effect observed as reduction or reverse in tumorigenic phenotype of tumor cells in an individual when a therapeutically effective amount of a compound is administered to an individual who is susceptible to or suffering from p185-mediated tumors. Therapeutically effective amounts are typically determined by the effect they have compared to the effect observed when a composition which includes no active ingredient is administered to a similarly situated individual.

As used herein, the term "high risk individual" is meant to refer to an individual who has had a erbB-2-associated tumor either removed or enter remission and who is therefore susceptible to a relapse or recurrence. As part of a treatment regimen for a high risk individual, the individual can be prophylactically treated to conduct the recurrence of the erbB-2-associated tumors. Thus, once it is known that an individual has had cancer characterized by tumor cells with p185 on their cell surfaces, the individual can be treated according to the present invention to prevent normal cells from transforming into tumor cells.

As used herein, the term "preventing the development of tumors" is meant to refer to preventing the transformation of cells that are not fully transformed into tumor cells. Thus, the development of tumors refers to the transformation event which results in the loss of a more normal phenotype and the acquisition of a transformed phenotype. According to some aspects of the present invention, compounds may be administered to individuals who are at risk of developing tumors. The prophylactic administration of compounds of the invention to high risk individuals results in the prevention of the transformation event occurring. Cells having the more normal phenotype are not converted to the cells having transformed phenotype. The compounds of the invention prevent tumors before they are formed by preventing a cell that are not fully transformed from becoming a cancer cell.

As used herein, the term "prophylactically effective amount" is meant to refer to an amount of a compound which produces a medicinal effect observed as the prevention of cells that are not fully transformed from becoming transformed in an individual when a prophylactically effective amount of a compound is administered to an individual who is susceptible to p185-mediated tumors. Prophylactically effective amounts are typically determined by the effect they have compared to the effect observed when a composition which includes no active ingredient is administered to a similarly situated individual.

As used herein, the terms "conformationally restricted peptides", "constrained peptides" and "conformationally constrained peptides" are used interchangeably and are meant to refer to peptides which, for example through intramolecular bonds, are conformationally stable and remain in a sufficiently restricted conformation. The compounds have an affinity to p185 and, when bound to p185 as cells, a biologically active effect on cells that have a p185-mediated transformation phenotype.

As used herein, the terms "aromatic amino acids" and "aromatic amino acid residues" used interchangeably are meant to refer to phenylalanine and tyrosine.

As used herein, the term "exocyclic amino acid residue" is meant to refer to amino acid residues which are linked to cyclicized peptide but which are not within the portion of the peptide that makes up the circularized structure.

As used herein, the term "exocyclic portions" is meant to refer to an amino acid sequence having one or more amino acid residues which is linked to cyclicized peptide but which are not within the portion of the peptide that makes up the circularized structure.

As used herein, the term "linking moiety" is meant to refer to a molecular component or functional group which is capable of forming bonds with three amino acids. As used herein, the term "linking amino acid residue" is meant to refer to an amino acid residue that is a linking moiety.

As used herein, the terms "active sequence" and "active region" are used interchangeably and are meant to refer to the amino acid sequence of the portion of a compound of the invention that is directly interacts with p185, wherein the interaction is characterized by an affinity between the active portion and p185.

As used herein, the term "chelating linker" is meant to refer to chemical linkers which are used to conjugate an amino acid residue of a peptide sequence to a detectable or cytotoxic agent. Examples include the macrocyclic polyaminoacetate DOTA (1,4,7,10-tetraazacyclododecane-1,4,7,10-tetraacetic acid), and DTPA (diethylenetriamine pentaacetate).

"Tamoxifen" refers to tamoxifen citrate. Tamoxifen has a molecular weight of 563.62, the pKa' is 8.85, the equilibrium solubility in water at 37° C. is 0.5 mg/ml and in 0.02 N HCl at 37° C., it is 0.2 mg/ml.

Chemically, tamoxifen is the trans-isomer of a triphenylethylene derivative. The chemical name is (Z)2-[4-(1,2-diphenyl-1-butenyl) phenoxy]-N,N-dimethylethanamine 2-hydroxy-1,2,3-propanetricarboxylate (1:1).

Description

The present invention relates to constrained peptides that contain exocyclic portions including exocyclic amino acids that are aromatic amino acids as well as an active region which specifically binds to p185. U.S. Pat. No. 6,100,377 issued Aug. 8, 2000 and entitled "Constrained Peptides" is incorporated herein by reference in its entirety.

The present invention is useful to therapeutically treat an individual identified as suffering from erbB-2-associated tumors in order to reverse the transformed phenotype of the tumor cells. The present invention is useful to prophylactically treat an individual who is predisposed to develop erbB-2-associated tumors or who has had erbB-2-associated tumors and is therefore susceptible to a relapse or recurrence. The present invention is useful to detectably image tumors with respect to p185 on their surfaces. The present invention is useful to detect and quantify p185 on all surfaces. The present invention is also useful to target cytotoxic agents preferentially to tumor tissue as opposed to normal tissue.

The translation product of the erbB-2 oncogene is p185, a transmembrane glycoprotein having tyrosine kinase activity and a molecular weight of about 185,000 daltons as determined by carrying out electrophoresis on the glycoprotein and comparing its movement with marker proteins of known molecular weight. Experiments have shown that p185 forms homodimers with other p185 molecules or heterodimers with epidermal growth factor receptor (EGFR) and that these dimers exhibit elevated tyrosine kinase activity which brings about the transformed phenotype in cells having such dimers. It is believed that dimerization of p185 with other membrane bound receptors, such as other p185 molecules or EGFR, results in elevated levels of tyrosine kinase activity and the transformed phenotype.

According to the present invention, compounds bind to p185 and thereby prevent the dimerization with other membrane bound receptors by down modulation of their surface receptors. When bound to p185, the compounds of the invention induce internalization of the receptor which results in elimination or reduction of tyrosine kinase activity. The elimination or reduction of tyrosine kinase activity results in an elimination or reduction in cell proliferation levels and a non-transformed, quiescent phenotype. The compounds of the invention cause down-modulation of erbB-2 cell surface reception. When bound to p185, the compounds of the invention reverse the transformed state of such cells, resulting in decreasing the rate of transformation in cells showing intact non-activated tyrosine kinase receptors found in normal cells are not affected by the compounds of the invention and hence are non-toxic.

The compounds of the invention are therefore useful in the treatment of individuals suspected of having from p185-mediated tumors. When administered to individuals who have been thusly identified, the compounds of the invention bind to p185, thereby causing modulation of erbB-2 receptors. The p185 receptor bound to the compound internalizes and the internalization of the p185 receptor contributes to the decrease in tyrosine kinase activity of the p185 receptors. When the tyrosine kinase activity in the cell is reduced from the elevated levels associated with amplified or overexpressed p185, the cell becomes quiescent and displays a non-transformed phenotype.

The compounds of the invention are also useful in the prevention of p185-mediated tumor formation and therefore in the method of prophylactically treating high risk individuals from developing p185-mediated tumors. That is, the prophylactic administration of compounds of the invention results in the prevention of cells that overexpress p185 from becoming transformed. The cells in the individuals which would turn into tumors in an untreated individual never become fully transformed and never become tumors in individuals treated by the methods of the invention. It has been discovered that the stocastic appearance of tumors which appear following removal of tumors or remission can be prevented by administration of compounds of the invention. When administered to individuals who have been identified as being susceptible to or otherwise at risk of developing tumors, the compounds of the invention bind to p185, thereby preventing and cause the internalization of the receptor/compound complex. The p185 receptor bound to the compound internalizes and the bound p185 receptor does not contribute the elevation in tyrosine kinase activity associated with dimerized p185 receptors. The tyrosine kinase activity in the cell never become sufficiently elevated and the cell remains non-transformed.

In some embodiments, the compounds of the invention can be labeled or otherwise made detectable. As a detectable compound that binds to p185, the compounds are useful as imaging agents and reagents in diagnostic procedures that are used to identify a tumor as being a p185-associated tumor. Labeled compounds of the invention can be administered to individuals suspected of suffering from p185-associated tumors. The labeled compounds will bind to the high density of p185 on cells and thereby accumulate on p185-associated tumor cells. Using standard imaging techniques, the site of the tumors can be detected.

One aspect of the invention therefore relates to methods of imaging p185-associated tumors. Such methods comprise the steps of administering a detectable compound of the invention to an individuals who is suffering from or susceptible to erbB-2-associated cancer and detecting the location of the detectable compound within the body of the individual.

The compounds bind to p185 that is present on cell surfaces and are therefore useful as diagnostic/characterizing reagents in diagnostic kits. When a tissue sample from an individual is contacted with a compound of the invention, the compound will bind to the p185 present on cells. The level of p185 expression can be quantified. Labeled compounds of the invention are also useful as in vitro reagents to quantify the amount of p185 present in the cell. Such information indicates whether or not a tumor is p185 mediated and therefore, whether specific treatments should be used or avoided. Using standard techniques, samples believed to include tumor cells are obtained and contacted with labeled compounds of the active region of the invention. After removing any unbound labeled compounds, the quantity of labeled compound bound to the cell or the quantity of removed as unbound labeled compounds is determined. The information directly relates to the amount of p185 the cell expresses and thus can be used to determine whether a cell is over expressing p185. Overexpression of p185 indicates p185-mediated transformation. This information is useful in formulating the prognosis and course of treatment to be imposed on the individual. Kits of the invention comprise detectable compounds of the invention and instructions for performing assays of the invention. Optionally, kits may also contain one or more of the following: containers which comprise positive controls, containers which comprise negative controls, photographs of representative examples of positive results and photographs of representative examples of negative results.

According to some embodiments, the present invention provides peptides having Formula I $$R_1\text{—}R_2\text{—}R_3\text{—}R_4\text{—}R_5 \qquad (I)$$

wherein:
- $R_1$, is O-benzyloxy or 1–4 amino acid residues including at least one of tyrosine or phenylalanine;
- $R_2$ is a linking moiety which bonds with $R_1$, $R_3$ and $R_4$ such that a portion of said peptide is cyclicized;
- $R_3$ is 5 amino acids;
- $R_4$ is a linking moiety which bonds with $R_3$, $R_5$ and $R_2$ such that a portion of said peptide is cyclicized;
- $R_5$ is 1–13 amino acid residues and at least one of which is tyrosine or phenylalanine;
- wherein: $R_1$, $R_2$, $R_3$, $R_4$, and $R_5$ taken together, are 20 amino acids or less; and $R_3$ is has the formula:

$$R_{31}\text{—}R_{32}\text{—}R_{33}\text{—}R_{34}\text{—}R_{35};$$

wherein:
- $R_{31}$, is aspartic acid; $R_{32}$ is glycine;
- $R_{33}$ is phenylalanine, tyrosine, tryptophan, histidine, D-phenylalanine, D-tyrosine, D-tryptophan, or D-histidine;
- $R_{34}$ is tyrosine; and
- $R_{35}$ is alanine, glycine, proline, D-alanine, D-glycine, or D-proline; and the carboxy terminus of $R_5$ is either amidated or hydroxylated.

The primary function of $R_1$, in compounds of the present invention arises from the presence of at least one amino acid that contains an aromatic group: i.e., the presence of tyrosine or phenylalanine. The presence of the aromatic amino acid at position $R_1$, results in an increase affinity of the peptide to p185 and an attendant increase in activity of the compound. In embodiments where additional amino acid residues are present, they can present the aromatic amino acid in a more effective position to further increase the affinity and activity of the compound. Additional amino acids that may be present must not eliminate the effect that the aromatic amino acid has on affinity or activity. Examples of amino acid sequences which may be used as $R_1$ are disclosed in U.S. Pat. No. 6,100,377. In some embodiments, the additional amino acids are present as a site for linkage to detectable labels or moieties. In some embodiments, the additional amino acids are present as a site for dimerization with other peptides; either for formation of homodimers with each other or heterodimers with other peptides. In some preferred embodiments, $R_1$ is 1–4 amino acids. In some preferred embodiments, R is 4 amino acids. In some preferred embodiments, $R_1$ is 3 amino acids. In some preferred embodiments, $R_1$ is 2 amino acids. In some preferred embodiments, R, is 1 amino acid. In some preferred embodiments, $R_1$ consists of Phe, dPhe, Tyr, dTyr, Gly-Phe, Gly-dPhe, Gly-Tyr, Gly-dTyr, Ala-Phe, Ala-dPhe, Ala-Tyr, Ala-dTyr, Lys-Phe, Lys-dPhe, Lys-Tyr, Lys-dTyr, Gly-Gly-Phe, Gly-Gly-dPhe, Gly-Gly-Tyr, Gly-Gly-dTyr, Gly-Gly-Phe (SEQ ID NO: 1), Gly-Gly-Gly-dPhe (SEQ ID NO:2), Gly-Gly-Gly-Tyr (SEQ ID NO:3), Gly-Gly-Gly-dTyr (SEQ ID NO:4), Ser-Gly-Gly-Phe (SEQ ID NO:5), Ser-Gly-Gly-dPhe (SEQ ID NO:6), Ser-Gly-Gly-Tyr (SEQ ID NO:7), Ser-Gly-Gly-dTyr (SEQ ID NO:8), or O-Benzlyoxy. Contemplated equivalents include aromatic functional groups at $R_1$ which are not part of tyrosine or phenylalanine.

The function of $R_2$ is to form bonds with $R_1$ and $R_3$ as well as to form bonds with $R_4$ which cyclicize or otherwise conformationally restrict the molecule. Bonds between $R_2$ and $R_4$ cyclicize the molecule and thereby maintain $R_2^-R_3^-R_4$, and, specifically $R_3$, in a constrained conformation which produces the specific biologically active surface that has an affinity for and interacts with p185. Further, in such an arrangement $R_1$ becomes an exocyclic portion of the peptide. Accordingly, $R_2$ may be any moiety capable of forming bonds with $R_4$ as well as $R_1$ and $R_3$. $R_2$ is preferably an amino acid residue, most preferably cysteine. When both $R_2$ and $R_4$ are cysteine, the disulfide bonds form between the two cysteines cyclicize the molecule. It is contemplated that $R_2$ may any moiety that, together with $R_4$, will allow for the cyclization of the portion of the molecule that includes $R_1$—$R_2$—$R_3$—$R_4$—$R_5$ while rendering $R_1$ and $R_5$ exocyclic portions of the peptide. Those having ordinary skill in the art can readily prepare peptides according to the present invention in which $R_2$ and $R_4$ are moieties capable of forming bonds to each other. The cyclization of linear peptides using disulfide bonds between non-adjacent cysteines is well known. Similarly, other non-adjacent amino acid residues may be linked to cyclicize a peptide sequence and the means to do so are similarly well known. Other methods of cyclization include those described by Di Blasio, et al., (1993) *Biopolymers*, 33:1037–1049; Wood, et al., (1992) *J. Pep. Prot. Res.*, 39:533–539; Saragovi, et al., (1992) *Immunomethods*, 1:5–9; Saragovi, et al., (1991) *Science*, 253:792–795; Manning, et al., (1993) *Reg. Peptides*, 45:279–283; Hruby, (1993) *Biopolymers*, 33:10731082; Bach, et al., (1994) *New Adv. Peptidomimetics Small Mol. Design*, 1:1–26; and Matsuyama, et al., (1992) *J Bacteriol.*, 174:1769–1776, each of which are incorporated herein by reference.

$R_3$ is the active region of the compounds according to this aspect of the invention. In compounds of the invention, the functional groups of the active region are in a conformation which places them in a particular three dimensional arrangement that allows them to interact with the amino acids and functional groups thereon of p185 and to bind to p185 through such interactions. In peptide mimetics, the functional groups are provided in the active three dimensional arrangement but are connected to modified or different backbones.

In some preferred embodiments, $R_3$ is DGFYA (SEQ ID NO:9), DGYYA (SEQ ID NO: 10), DGWYA (SEQ ID NO: 11), DGHYA (SEQ ID NO: 12), DGdFYA (SEQ ID NO: 13), DGdYYA (SEQ ID NO: 14), DGdWYA (SEQ ID NO: 15), DGdHYA (SEQ ID NO: 16), DGFYdA (SEQ ID NO: 17), DGYYdA (SEQ ID NO: 18), DGWYdA (SEQ ID NO: 19), DGHYdA (SEQ ID NO:20), DGdFYdA (SEQ ID NO:21), DGdYYdA (SEQ ID NO:22). DGdWYdA (SEQ ID NO:23), DgdHYdA (SEQ ID NO:24), DGFYG (SEQ ID NO:25), DGYYG (SEQ ID NO:26), DGWYG,(SEQ ID NO:27) DGHYG (SEQ ID NO:28), DGdFYG (SEQ ID NO:29), DGdYYG (SEQ ID NO:30), DGdWYG (SEQ ID NO:31), DgdHYG (SEQ ID NO:32), DGFYP (SEQ ID NO:33), DGYYP (SEQ ID NO:34), DGWYP (SEQ ID NO:35), DGHYP (SEQ ID NO:36), DGdFYP (SEQ ID NO:37), DGdYYP (SEQ ID NO:38), DGdWYP (SEQ ID NO:39), DGdHYP (SEQ ID NO:40), DGFYdP (SEQ ID NO:41), DGYYdP (SEQ ID NO:42), DGWYdP (SEQ ID NO:43), DGHYdP (SEQ ID NO:44), DGdFYdP (SEQ ID NO:45), DGdYYdP (SEQ ID NO:46), DGdWYdP (SEQ ID NO:47), or DGdHYdP (SEQ ID NO:48).

The function of $R_4$ is to form bonds with $R_2$ which cyclicize or otherwise conformationally restrict the molecule. Bonds between $R_4$ and $R_2$ cyclicize the molecule and thereby maintain $R_2$—$R_3$—$R_4$, and, specifically $R_3$, in a constrained conformation which produces the specific biologically active surface that has an affinity for and interacts with p185. Accordingly, $R_4$ may be any moiety capable of forming bonds with $R_2$ as well as $R_3$ and $R_5$. $R_4$ is preferably an amino acid residue, most preferably cysteine. When both $R_5$ and $R_2$ are cysteine, disulfide bonds formed between the two cysteines cyclicizes the molecule. It is contemplated that $R_4$ may be any moiety that, together with $R_2$, will allow for the cyclization of the molecule. Those having ordinary skill in the art can readily prepare peptides according to the present invention in which $R_2$ and $R_4$ are moieties capable of forming bonds to each other. The cyclization of linear peptides using disulfide bonds between non-adjacent cysteines is well known. Similarly, other non-adjacent amino acid residues may be linked to cyclicize a peptide sequence and the means to do so are similarly well known. Other methods of cyclization include those described by Di Blasio, et al., (1993) *Biopolymers*, 33:1037–1049; Wood, et al., (1992) *J. Pep. Prot. Res.*, 39:533–539; Saragovi, et al., (1992) *Immunomethods*, 1:5–9; Saragovi, et al., (1991) *Science*, 253:792–795; Manning, et al., (1993) *Reg. Peptides*, 45:279–283; Hruby, (1993) *Biopolymers*, 33:1073–1082; Bach, et al., (1994) *New Adv. Peptidomimetics Small Mol. Design*, 1:1–26; and Matsuyama, et al., (1992) *J. Bacteriol.*, 174:1769–1776, each of which are incorporated herein by reference.

The primary function of $R_5$ in compounds of the present invention arises from the presence of at least one amino acid that contains an aromatic group: i.e. the presence of tyrosine or phenylalanine. The presence of the aromatic amino acid at position $R_5$ results in an increase affinity of the peptide to p185 and an attendant increase in activity of the compound. In embodiments where additional amino acid residues are present, they can present the aromatic amino acid in a more effective position to further increase the affinity and activity of the compound. Additional amino acids that may be present must not eliminate the effect that the aromatic amino acid has on affinity or activity. Examples of amino acid sequences which may be used as $R_5$ are disclosed in U.S. Pat. No. 6,100,377. In some embodiments, the additional amino acids are present as a site for linkage to detectable labels or moieties. In some embodiments, the additional amino acids are present as a site for dimerization with other peptides; either for formation of homodimers with each other or heterodimers with other peptides In some preferred embodiments, $R_5$ is 1–13 amino acids. In some preferred embodiments, $R_5$ is 12 amino acids. In some preferred embodiments, $R_5$ is 11 amino acids. In some preferred embodiments, $R_5$ is 10 amino acids. In some preferred embodiments, $R_5$ is 9 amino acids. In some preferred embodiments, $R_5$ is 8 amino acids. In some preferred embodiments, $R_2$ is 7 amino acids. In some preferred embodiments, $R_5$ is 6 amino acids. In some preferred embodiments, $R_5$ is 5 amino acids. In some preferred embodiments, $R_2$ is 4 amino acids. In some preferred embodiments, $R_5$ is 3 amino acids. In some preferred embodiments, $R_5$ is 2 amino acids. In some preferred embodiments, $R_5$ is 1 amino acid. In some preferred embodiments, $R_5$ is selected from the group consisting of YMDV (SEQ ID NO:49), dYMDV (SEQ ID NO:50), FMDV (SEQ ID NO:51), dFMDV (SEQ ID NO:52) YKDV (SEQ ID NO:53), dYKDV (SEQ ID NO:54), FKDV (SEQ ID NO:55), dFKDV (SEQ ID NO:56), YMDVK (SEQ ID NO:57), dYMDVK (SEQ ID NO:58), FMDVK,(SEQ ID NO:59) dFMDVK (SEQ ID NO:60), YKDVK (SEQ ID NO:61), dYKDVK (SEQ ID NO:62), FKDVK (SEQ ID NO:63), dFKDVK (SEQ ID NO:64), YMDVG (SEQ ID NO:65), dYMDVG (SEQ ID NO:66), FMDVG (SEQ ID NO:67), dFMDVG (SEQ ID NO:68), YKDVG (SEQ ID NO:69), dYKDVG (SEQ ID NO:70), FKDVG (SEQ ID NO:71), dFKDVG (SEQ ID NO:72), YMDVKG (SEQ ID NO:73), dYMDVKG (SEQ ID NO:74), FMDVKG (SEQ ID NO:75), dFMDVKG (SEQ ID NO:76), YKDVKG (SEQ ID NO:77), dYKDVKG (SEQ ID NO:78), FKDVKG (SEQ ID NO:79), dFKDVKG (SEQ ID NO:80), YMDVGG (SEQ ID NO:81), dYMDVGG (SEQ ID NO:82), FMDVGG (SEQ ID NO:83), dFMDVGG (SEQ ID NO:84), YKDVGG (SEQ ID NO:85), dYKDVGG (SEQ ID NO:86), FKDVGG (SEQ ID NO:87), dFKDVGG (SEQ ID NO:88), YMDVKGG (SEQ ID NO:89), dYMDVKGG (SEQ ID NO:90), FMDVKGG (SEQ ID NO:91), dFMDVKGG (SEQ ID NO:92), YKDVKGG (SEQ ID NO:93), dYKDVKGG,(SEQ ID NO:94) FKDVKGG (SEQ ID NO:95), dFKDVKGG (SEQ ID NO:96), YMDVGGS (SEQ ID NO:97), dYMDVGGS (SEQ ID NO:98), FMDVGGS (SEQ ID NO:99), dFMDVGGS (SEQ ID NO:100), YKDVGGS (SEQ ID NO:101), dYKDVGGS (SEQ ID NO:102), FKDVGGS (SEQ ID NO: 103), dFKDVGGS (SEQ ID NO: 104), YMDVKGGS (SEQ ID NO:105), dYMDVKGGS (SEQ ID NO:106), FMDVKGGS (SEQ ID NO:107), dFMDVKGGS (SEQ ID NO: 108), YKDVKGGS (SEQ ID NO: 109), dYKDVKGGS (SEQ ID NO: 10), FKDVKGGS (SEQ ID NO: 111), or dFKDVKGGS (SEQ ID NO: 112). In some preferred embodiments, $R_5$ is selected from the group consisting of $Y^-R_{51}$, $dY-R_{51}$, $F-R_{51}$, or $dF-R_51$, wherein $R_{51}$, is any long aliphatic chain of d and/or l amino acids. In some preferred embodiments, $R_5$ is selected from the group consisting of $Y^-R_{51}$, $dY-R_{51}$, $F^-R_{51}$, or $dF^-R_{51}$, wherein $R_{51}$, is an amino acid chain comprising up to 12 amino acids independently selected from the group consisting of Lys, Leu and Ile.

In some preferred embodiments, $R_1$ and $R_5$ collectively contain both tyrosine and phenylalanine. That is, if $R_1$ comprises tyrosine then $R_5$ comprises phenylalanine and if $R_1$ comprises phenylalanine then $R_5$ comprises tyrosine. In some preferred embodiments, $R_1$ and $R_5$ do not both contain tyrosine or phenylalanine. That is, if $R_1$ comprises tyrosine and not phenylalanine then $R_{55}$ comprises phenylalanine and not tyrosine and if $R_1$ comprises phenylalanine and not tyrosine then $R_5$ comprises tyrosine and not phenylalanine.

In some preferred embodiments, $R_1$, $R_2$, $R_3$, $R_4$ and $R_5$, taken together, are less than 20 amino acids. In some preferred embodiments, $R_1$, $R_2$, $R_3$, $R_4$ and $R_5$, taken together, are 19 amino acids or less. In some preferred embodiments, $R_1$, $R_2$, $R_3$, $R_4$ and $R_5$, taken together, are less than 18 amino acids. In some preferred embodiments, $R_1$, $R_2$, $R_3$, $R_4$ and $R_5$, taken together, are 17 amino acids. In some preferred embodiments, $R_1$, $R_2$, $R_3$, $R_4$ and $R_5$, taken together, are less than 16 amino acids. In some preferred embodiments, $R_1$ $R_2$, $R_3$, $R_4$ and $R_5$, taken together, are less than 15 amino acids. In some preferred embodiments, $R_1$ $R_2$, $R_3$, $R_4$ and $R_5$, taken together, are 14 amino acids. In some preferred embodiments, $R_1$ $R_2$, $R_3$, $R_4$ and $R_5$, taken together, are 13 amino acids. In some preferred embodiments, $R_1$ $R_2$, $R_3$, $R_4$ and $R_5$, taken together, are 12 amino acids. In some preferred embodiments, $R_1$ $R_2$, $R_3$, $R_4$ and $R_5$, taken together, are 11 amino acids. In some preferred embodiments, $R_1$ $R_2$, $R_3$, $R_4$ and $R_5$, taken together, are 10 amino acids.

In some embodiments, the peptide is selected from the group consisting of: YCDGFYACYMDV-NH$_2$ (SEQ ID NO: 113), YCDGFYACYMDV-OH (SEQ ID NO: 114), GYCDGFYACYMDV (SEQ ID NO: 115), GGYCDGFYA-CYMDV (SEQ ID NO: 116), GGGYCDGFYACYMDV (SEQ ID NO:117), dFCDGFYACdYMDV-NH$_2$ (SEQ ID NO: 118), dFCDGFYACdYMDV-OH (SEQ ID NO: 119), GdFCDGFYACdYMDV (SEQ ID NO: 120), GGdFCDG-FYACdYMDV (SEQ ID NO: 121), GGGdFCDGFY-ACdYMDV (SEQ ID NO: 122), FCDGFYACYMDVK-NH$_2$ (SEQ ID NO: 123), dFCDGFYACdYMDVK-OH (SEQ ID NO: 124), GdFCDGFYACdYMDVK (SEQ ID NO: 125), GGdFCDGFYACdYMDVK (SEQ ID NO: 126), GGGdFCDGFYACdYMDVK (SEQ ID NO: 127), FCDGFYACYKDV-NH$_2$ (SEQ ID NO: 128), FCDGFYACYKDV-OH (SEQ ID NO:129), GFCDGFYA-CYMDV (SEQ ID NO:130), GGFCDGFYACYKDV (SEQ ID NO: 131), GGGFCDGFYACYKDV (SEQ ID NO: 132), GFCDGFYACYMDV-NH$_2$ (SEQ ID NO: 133), GFCDGFYACYMDV-OH (SEQ ID NO: 134), GFCDG-FYACYMDVG (SEQ ID NO: 135), GFCDGFYACdYMD-VGG (SEQ ID NO: 136), and GFCDGFYACdYMDVGGG (SEQ ID NO: 137).

In some embodiments, the peptide is according to Formula I except YCDGFYACYMDV-NH$_2$ (SEQ ID NO:113), dFCDGFYACdYMDV-NH$_2$ (SEQ ID NO: 118), FCDGFYACYMDVK-NH$_2$ (SEQ ID NO: 123), FCDGFYACYKDV-OH (SEQ ID NO: 129), and GFCDGFYACYMDV-OH (SEQ ID NO: 134).

According to some embodiments, the present invention provides peptides having Formula II:

$$R_6—R_7—R_8—R_9—R_{10} \qquad (II)$$

wherein $R_6$ is 1–4 amino acid residues including at least one of tyrosine or phenylalanine;

$R_7$ is cysteine;

$R_8$ is 5–7 amino acids;

$R_9$ is cysteine;

$R_{10}$ is 1–13 amino acid residues and at least one of which is tyrosine or phenylalanine;

wherein: $R_6$, $R_7$, $R_8$, $R_9$, and $R_{10}$ taken together, are 20 amino acids or less; and $R_8$ has the formula $$R_{81}—R_{82}—R_{83}$$

wherein $R_{81}$ is glycine-aspartic acid, proline-aspartic acid, or aspartic acid;

$R_{82}$ is glycine, proline or proline-proline; and $R_{83}$ is phenylalanine-tyrosine-alanine;

and the carboxy terminus of $R_{10}$ is either amidated or hydroxylated.

In some preferred embodiments, $R_6$ consists of Phe, dPhe, Tyr, dTyr, Gly-Phe, Gly-dPhe, Gly-Tyr, Gly-dTyr, Ala-Phe, Ala-dPhe, Ala-Tyr, Ala-dTyr, Lys-Phe, Lys-dPhe, Lys-Tyr, Lys-dTyr, Gly-Gly-Phe, Gly-Gly-dPhe, Gly-Gly-Tyr, Gly-Gly-dTyr, Gly-Gly-Gly Phe (SEQ ID NO: 1), Gly-Gly-Gly-dPhe (SEQ ID NO:2), Gly-Gly-Gly-Tyr (SEQ ID NO:3), Gly-Gly-Gly-dTyr (SEQ ID NO:4), Ser-Gly-Gly-Phe (SEQ ID NO:5), Ser-Gly-Gly-dPhe (SEQ ID NO:6), Ser-Gly-Gly-Tyr (SEQ ID NO:7), or Ser-Gly-Gly-dTyr (SEQ ID NO:8). Contemplated equivalents include aromatic functional groups at $R_1$ which are not part of tyrosine or phenylalanine. $R_6$ is preferably phenylalanine in some preferred embodiments.

In some preferred embodiments, $R_8$ has the formula $$R_{81}—R_{82}—R_{83}$$

wherein $R_{81}$ is glycine-aspartic acid, proline-aspartic acid, or aspartic acid;

$R_{82}$ is glycine, proline or proline-pro line; and $R_{83}$ is phenylalanine-tyrosine-alanine.

In some preferred embodiments, $R_8$ consists of GDGFYA (SEQ ID NO: 138), GDGFYA (SEQ ID NO: 139), DPFYA (SEQ ID NO: 140), PDGFYA (SEQ ID NO: 141), or DPPFYA (SEQ ID NO: 142).

In some preferred embodiments, $R_{10}$ is selected from the group consisting of YMDV (SEQ ID NO:49), dYMDV (SEQ ID NO:50), FMDV (SEQ ID NO:51), dFMDV (SEQ ID NO:52) YKDV (SEQ ID NO:53), dYKDV (SEQ ID NO:54), FKDV (SEQ ID NO:55), dFKDV (SEQ ID NO:56), YMDVK (SEQ ID NO:57), dYMDVK (SEQ ID NO:58), FMDVK,(SEQ ID NO:59) dFMDVK (SEQ ID NO:60), YKDVK (SEQ ID NO:61), dYKDVK (SEQ ID NO:62), FKDVK (SEQ ID NO:63), dFKDVK (SEQ ID NO:64), YMDVG (SEQ ID NO:65), dYMDVG (SEQ ID NO:66), FMDVG (SEQ ID NO:67), dFMDVG (SEQ ID NO:68), YKDVG (SEQ ID NO:69), dYKDVG (SEQ ID NO:70), FKDVG (SEQ ID NO:71), dFKDVG (SEQ ID NO:72), YMDVKG (SEQ ID NO:73), dYMDVKG (SEQ ID NO:74), FMDVKG (SEQ ID NO:75), dFMDVKG (SEQ ID NO:76), YKDVKG (SEQ ID NO:77), dYKDVKG (SEQ ID NO:78), FKDVKG (SEQ ID NO:79), dFKDVKG (SEQ ID NO: 80), YMDVGG (SEQ ID NO: 81), dYMDVGG (SEQ ID NO: 82), FMDVGG (SEQ ID NO:83), dFMDVGG (SEQ ID NO:84), YKDVGG (SEQ ID NO:85), dYKDVGG (SEQ ID NO:86), FKDVGG (SEQ ID NO:87), dFKDVGG (SEQ ID NO:88), YMDVKGG (SEQ ID NO:89), dYMDVKGG (SEQ ID NO:90), FMDVKGG (SEQ ID NO:91), dFMD-VKGG (SEQ ID NO:92), YKDVKGG (SEQ ID NO:93), dYKDVKGG,(SEQ ID NO:94) FKDVKGG (SEQ ID NO:95), dFKDVKGG (SEQ ID NO:96), YMDVGGS (SEQ ID NO:97), dYMDVGGS (SEQ ID NO:98), FMDVGGS (SEQ ID NO:99), dFMDVGGS (SEQ ID NO: 100), YKD-VGGS (SEQ ID NO: 101), dYKDVGGS (SEQ ID NO: 102), FKDVGGS (SEQ ID NO: 103), dFKDVGGS (SEQ ID NO: 104), YMDVKGGS (SEQ ID NO:105), dYMD-VKGGS (SEQ ID NO:106), FMDVKGGS (SEQ ID NO:107), dFMDVKGGS (SEQ ID NO: 108), YKDVKGGS (SEQ ID NO: 109), dYKDVKGGS (SEQ ID NO: 110), FKDVKGGS (SEQ ID NO: 111), or dFKDVKGGS (SEQ ID NO: 112). In some preferred embodiments, $R_{10}$ is: YMDV (SEQ ID NO:49).

In some embodiments, the peptide is selected from the group consisting of: FCGDGFYACYMDV-NH$_2$ (SEQ ID NO: 143), FCGDGFYACYMDV-OH (SEQ ID NO: 144), FCDGFYACYMDV-NH$_2$ (SEQ ID NO: 145), FCDGFYACYMDV-OH (SEQ ID NO: 146), FCDPFYACYMDV-NH$_2$ (SEQ ID NO:147), FCDPFYACYMDV-OH [(SEQ ID NO: 147)] (SEQ ID NO:152), FCPDGFYACYMDV-NH$_2$ (SEQ ID NO: 148), FCPDGFYACYMDV-OH (SEQ ID NO: 149), FCDPPFYACYMDV-NH$_2$ (SEQ ID NO: 150), and FCDPPFYACYMDV-OH (SEQ ID NO: 151). In some embodiments, the peptide is according to Formula II except FCGDGFYACYMDV-NH$_2$ (SEQ ID NO: 143), FCGDGFYACYMDV-OH (SEQ ID NO: 144), FCDGFYACYMDV-NH$_2$ (SEQ ID NO: 145), FCDGFYACYMDV-OH (SEQ ID NO: 146), FCDPFYACYMDV-NH$_2$ (SEQ ID NO:152), FCDPFYACYMDV-OH (SEQ ID NO: 147),
FCPDGFYACYMDV-NH$_2$ (SEQ ID NO: 148),
FCPDGFYACYMDV-OH (SEQ ID NO: 149),
FCDPPFYACYMDV-NH$_2$ (SEQ ID NO: 150), and
FCDPPFYACYMDV-OH (SEQ ID NO: 151).

Those having ordinary skill in the art can readily construct molecules according Formula I or Formula II and determine whether or not the compounds are active as p185 binding compounds which prevent and eliminate the p185-mediated transformation phenotype.

The peptides of the invention may be dimerized, with each other to form homodimers or with other compounds including compounds of the invention to form heterodimers. In preferred dimers, the residues involved in the chemical bound which links the monomers is in the R$_1$ position of the compounds of the invention.

The compositions used in the method of treating, preventing or imaging tumors or quantifying p185 may comprise mimetics instead of peptides. As used herein, the term "Mimetics" is used to refer to compounds which mimic the activity of peptide. Mimetics are non-peptides but may comprise amino acids linked by non-peptide bonds. Parent application U.S. Pat. No. 5,677,637 issued Jun. 10, 1997 and parent applications thereof, all of which are incorporated herein by reference, contain detailed guidance on the production of mimetics. Briefly, the three dimensional structure of the peptides which specifically interacts with the three dimensional structure of the p185 is duplicated by a molecule that is not a peptide.

The compounds of the invention may be used to treat individuals suffering from p185-associated tumors. According to one aspect of the invention, compounds are administered to individuals suspected of having p185 tumors. Those having ordinary skill in the art can readily determine whether an individual may have a tumor likely to be a p185-associated tumor. Biopsy protocols can be performed to identify tumor samples and determine whether or not they are p185 associated tumors. The diagnostic/characterization protocol described above may be used in the characterization and determination of p185 levels present on cell samples.

The compounds of the invention may be used to prevent the occurrence of p185 associated tumors in individuals susceptible to p185-associated tumors. According to one aspect of the invention, compounds are administered prophylactically to individuals susceptible to developing p185 tumors. Those having ordinary skill in the art can readily determine whether an individual may be susceptible to p185 associated tumors. The invention is particularly useful in high risk individuals who, for example, have a family history of erbB-2-associated cancer or show a genetic predisposition. Additionally, the present invention is particularly useful to prevent patients who have had erbB-2-associated tumors removed by surgical resection or who have been diagnosed as having erbB-2-associated cancer in remission.

Methods of the present invention comprise administering a single or multiple doses of the compounds of the invention. Preferred for human pharmaceutical use are pharmaceutical compositions that comprise the compounds of the present invention in combination with a pharmaceutically acceptable carrier or diluent.

The pharmaceutical compositions of the present invention may be administered by any means that enables the active agent to reach the agent's site of action in the body of a mammal. In the case of the peptides of the invention, the primary focus is the ability to reach and bind with cellular p185. Because proteins are subject to being digested when administered orally, parenteral administration, i.e., intravenous, subcutaneous, intramuscular, would ordinarily be used to optimize absorption. These small compact forms are resistant to many proteases and should be orally available.

In one aspect, the compounds of the present invention are administered in combination with other cancer therapeutics used to treat c-erbB-2-associated tumors, such as Herceptin or tamoxifen.

In addition to pharmaceutical compositions which comprise compounds of the invention, alone or in combination with other cancer therapeutics, therapeutic and diagnostic pharmaceutical compositions of the present invention include conjugated compounds specifically targeted to p185. The pharmaceutical compositions which comprise conjugated compositions of the present invention may be used to diagnose or treat individuals suffering from p185-associated cancer.

One aspect of the present invention relies upon the use of a compound of the invention conjugated to a detectable and/or cytotoxic agent. In conjugated compositions, the compound of the invention delivers the active agent to cells that have p185. Thus, cells which overexpress p185 will be contacted with more active agents than other cells. The active agent is useful to image, inhibit proliferation of and/or kill the cell. According to one aspect of the present invention, the active agent is a therapeutic agent or an imaging agent. In a preferred embodiment, the imaging agent is $^{99m}$Tc, chemically conjugated to the peptides of the present invention using, e.g., DOTA and DTPA.

Some chemotherapeutic agents may be used as active agents and conjugated with compounds of the invention. Chemotherapeutics are typically, small chemical entities produced by chemical synthesis and include cytotoxic drugs, cytostatic drugs as well as compounds which affects cells in other ways such as reversal of the transformed state to a differentiated state or those which inhibit cell replication. Examples of chemotherapeutics include, but are not limited to: methotrexate (amethopterin), doxorubicin (adrimycin), daunorubicin, cytosinarabinoside, etoposide, 5–4 fluorouracil, melphalan, chlorambucil, and other nitrogen mustards (e.g., cyclophosphamide), cis-platinum, vindesine (and other vinca alkaloids), mitomycin and bleomycin.

Active agents may be toxins: complex toxic products of various organisms including bacteria, plants, etc. Examples of toxins include but are not limited to: ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. Protein toxins may be produced using recombinant DNA techniques as fusion proteins which include peptides of the invention. Protein toxins may also be conjugated to compounds of the invention by non-peptidyl bonds.

Radioisotopes may be conjugated to compounds of the invention to provide compositions that are useful as therapeutic agents or for imaging procedures. Examples of radioisotopes which useful in radiation therapy include: $^{47}$Sc, $^{67}$Cu, $^{90}$Y, $^{109}$Pd, $^{123}$I $^{125}$I, $^{131}$I, $^{186}$Re, $^{188}$Re, $^{199}$Au, $^{211}$At, $^{212}$Pb, $^{212}$Bi. Example of radioisotopes useful in imaging procedures include: $^{43}$K, $^{52}$Fe, $^{57}$Co, $^{67}$Cu, $^{67}$Ga, $^{68}$Ga, $^{77}$Br, $^{81}$Rb/$^{81m}$Sr, $^{87m}$Sr, $^{99}$Tc, $^{111}$In, $^{113m}$I, $^{123}$I, $^{125}$I, $^{127}$Cs, $^{129}$Cs, $^{131}$I, $^{197}$Hg, $^{203}$Pb and $^{206}$Bi. Preferred radiostopes are Tc, particularly $^{99m}$Tc, Y, particularly $^{90}$Y, and $^{18}$F.

Imaging agents are useful in diagnostic procedures as well as the procedures used to identify the location of p185 associated tumors. Imaging can be performed by many procedures well-known to those having ordinary skill in the art and the appropriate imaging agent useful in such procedures may be conjugated to compounds of the invention by well-known means. Imaging can be performed, for example, by radioscintigraphy, nuclear magnetic resonance imaging (MRI) or computed tomography (CT scan). The most commonly employed radiolabels for imaging agents include radioactive iodine and indium. Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium.

Radiolabels are conjugated to compounds of the invention by a variety of well-known techniques readily performed without undue experimentation by those having ordinary skill in the art. Radiolabels retain their radioactivity irrespective of conjugation. Conjugation may be accomplished directly between the compound and the radioisotope or linking, intermediate molecular groups may be provided between the compound and the radioisotope. Crosslinkers are particularly useful to facilitate conjugation by providing attachment sites for each moiety. Crosslinkers may include additional molecular groups which serve as spacers to separate the moieties from each other to prevent either from interfering with the activity of the other. Often imaging can be imaged using fluorescein, which are activated by light. (e.g. fluorescein (green), phycoerythrin (orange), P-E-cyanine-5 (red), P-E-texas red (red), cyanine-3 (orange), cyananine-5 (red), AMCA (ultraviolet detection). Examples of crosslinkers include DOTA/DTPA.

One having ordinary skill in the art may conjugate a compound of the invention to a chemotherapeutic drug using well-known techniques. For example, Magerstadt, M. *Antibody Conjugates and Malignant Disease.* (1991) CRC Press, Boca Raton, USA, pp. 110 152) which is incorporated herein by reference, teaches the conjugation of various cytostatic drugs to amino acids of antibodies. Such reactions may be applied to conjugate chemotherapeutic drugs to the compounds of the invention. Compounds of the invention such as peptides which have a free amino group may be conjugated to active agents at that group. Most of the chemotherapeutic agents currently in use in treating cancer possess functional groups that are amenable to chemical crosslinking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of a compound of the invention.

Pharmaceutical compositions of the present invention may be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results.

Dosage forms (composition) suitable for internal administration generally contain from about 1 milligram to about 500 milligrams of active ingredient per unit. In these pharmaceutical compositions the active ingredient will ordinarily be present in an amount of about 0.5–95 by weight based on the total weight of the composition.

Because conjugated compounds are specifically targeted to cells with p185, conjugated compounds which comprise chemotherapeutics or toxins are administered in doses less than those which are used when the chemotherapeutics or toxins are administered as unconjugated active agents, preferably in doses that contain up to 100 times less active agent. In some embodiments, conjugated compounds which comprise chemotherapeutics or toxins are administered in doses that contain 10–100 times less active agent as an active agent than the dosage of chemotherapeutics or toxins administered as unconjugated active agents. To determine the appropriate dose, the amount of compound is preferably measured in moles instead of by weight. In that way, the variable weight of different compounds of the invention does not affect the calculation. Presuming a one to one ratio of p185-binding compound to active agent in conjugated compositions of the invention, less moles of conjugated compounds may be administered as compared to the moles of unconjugated compounds administered, preferably up to 100 times less moles.

For parenteral administration, the compound can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of *Remington's Pharmaceutical Sciences*, A. Osol, a standard reference text in this field.

For example, a parenteral composition suitable for administration by injection is prepared by dissolving 1.5% by weight of active ingredient in 0.9% sodium chloride solution.

According to the present invention, the compound may be administered to tissue of an individual by topically or by lavage. The compounds may be formulated as a cream, ointment, salve, douche, suppository or solution for topical administration or irrigation. Formulations for such routes administration of pharmaceutical compositions are well known. Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation. The pharmaceutical preparations according to the present invention are preferably provided sterile and pyrogen free.

One of skill in the art of pharmaceutical formulations, e.g., having an advanced degree in Pharmaceutics or Pharmaceutical Sciences, can prepare a variety of appropriate dosage forms and formulations for the compositions of the invention with no more than routine experimentation. A number of texts in the field, a,g., *Remington's Pharmaceutical Sciences* and *The U.S. Pharmacopoeia/National Formulary*, latest editions, provide considerable guidance in this respect.

A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

The compositions may include additional components to render them more effective. For example, a composition of the invention may comprise multiple anti-p185 compounds. The compositions may include other anti-cancer agents such as, for example, cis-platin, methotrexate, and/or G-MCSF. Such compositions would be particularly useful for administration to patients diagnosed and treated for erbB-2-associated cancer.

Administration Regimen

About 5 µg to 5000 mg of peptide may be administered. In some preferred embodiments, 50, µg to 500 mg of peptide may be administered. In other preferred embodiments, 500 µg to 50 mg of peptide may be administered. In a preferred embodiment, 5 mg of peptide is administered.

Prophylactic compositions may be administered by an appropriate route such as, for example, by oral, intranasal, intramuscular, intraperitoneal or subcutaneous administration. In some embodiments, intravenous administration is preferred.

Subsequent to initial administration, individuals may be boosted by readministration. In some preferred embodiments, multiple administrations are performed.

EXAMPLES

The present invention is further described by means of the example, presented below. The use of such an example is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

A peptide is selected from the group consisting of: YCDGFYACYMDV-NH$_2$ (SEQ ID NO: 113), YCDGFYACYMDV-OH (SEQ ID NO: 114), GYCDGFYACYMDV (SEQ ID NO: 115), GGYCDGFYACYMDV (SEQ ID NO: 116), GGGYCDGFYACYMDV (SEQ ID NO: 117), dFCDGFYACdYMDV-NH$_2$ (SEQ ID NO: 118), dFCDGFYACdYMDV-OH (SEQ ID NO:119), GdFCDGFYACdYMDV (SEQ ID NO:120), GGdFCDGFYACdYMDV (SEQ ID NO:121), GGGdFCDGFYACdYMDV (SEQ ID NO: 122), FCDGFYACYMDVK-NH$_2$ (SEQ ID NO: 123), dFCDGFYACdYMDVK-OH (SEQ ID NO: 124), GdFCDGFYACdYMDVK (SEQ ID NO: 125), GGdFCDGFYACdYMDVK (SEQ ID NO: 126), GGGdFCDGFYACdYMDVK (SEQ ID NO: 127), FCDGFYACYKDV-NH$_2$ (SEQ ID NO: 128), FCDGFYACYKDV-OH (SEQ ID NO: 129), GFCDGFYACYKDV (SEQ ID NO: 130), GGFCDGFYACYKDV (SEQ ID NO: 131), GGGFCDGFYACYKDV (SEQ ID NO: 132), GFCDGFYACYMDV-NH$_2$ (SEQ ID NO: 133), GFCDGFYACYMDV-OH (SEQ ID NO: 134), GFCDGFYACYMDVG (SEQ ID NO:135), GFCDGFYACdYMDVGG (SEQ ID NO: 136), and GFCDGFYACdYMDVGGG (SEQ ID NO: 137) and conjugated to radioisotopes of Tc, particularly $^{99M}$Tc, Y, particularly $^{90}$Y, and $^{18}$F using as linkers between the radionuclides and peptides, DOTA/DTPA or DOTA/DTPA-glycine, DOTA/DTPA-glycine-glycine, or DOTA/DTPA-glycine-glycine-glycine.

Example 2

A peptide is selected from the group consisting of: FCGDGFYACYMDV-NH$_2$ (SEQ ID NO: 143), FCGDGFYACYMDV-OH (SEQ ID NO: 144), FCDGFYACYMDV-NH$_2$ (SEQ ID NO: 145), FCDGFYACYMDV-OH (SEQ ID NO: 146), FCDPFYACYMDV-NH$_2$ (SEQ ID NO: 147), FCDPFYACYMDV-OH [(SEQ ID NO: 147)] (SEQ ID NO:152), FCPDGFYACYMDV-NH$_2$ (SEQ ID NO: 148), FCPDGFYACYMDV-OH (SEQ ID NO: 149), FCDPPFYACYMDV-NH$_2$ (SEQ ID NO: 150), and FCDPPFYACYMDV-OH (SEQ ID NO: 151). In some embodiments, the peptide is according to Formula II except FCGDGFYACYMDV-NH, (SEQ ID NO: 143), FCGDGFYACYMDV-OH (SEQ ID NO: 1. 44), FCDGFYACYMDV-NH$_2$(SEQ ID NO: 145), FCDGFYACYMDV-OH (SEQ ID NO: 146), FCDPFYACYMDV-NH, (SEQ ID NO: 147), FCDPFYACYMDV-OH (SEQ ID NO:152), FCPDGFYACYMDV-NH$_2$ (SEQ ID NO: 148), FCPDGFYACYMDV-OH (SEQ ID NO: 149), FCDPPFYACYMDV-NH$_2$, (SEQ ID NO: 150), and FCDPPFYACYMDV-OH (SEQ ID NO: 151) and conjugated to radioisotopes of Tc, particularly $^{90M}$Tc, Y, particularly $^{90}$Y, and $^{18}$F using as linkers between the radionuclicles and peptides, DOTA/DTPA or DOTA/DTPA-glycine, DOTA/DTPA-glycine-glycine, or DOTA/DTPA-glycine-glycine-glycine.

Example 3

Overexpression of the HER2 receptor is observed in about 30% of breast and ovarian cancers and is often associated with an unfavorable prognosis. An anti-HER2 peptide (AHNP) based on the structure of the CDR-H3 loop of the anti-HER2 rhumAb 4D5 was designed and showed that this peptide can mimic some functions of rhumAb45. The peptide disabled HER2 tyrosine kinases in vitro and in vivo similar to the monoclonal antibody (Park, B.-W. et al. *Nat. Biotechnol.* 2000, 18, 194–198). AHNP has been shown to selectively bind to the extracellular domain of the HER2 receptor with a submicromolar affinity in Biacore assays. In addition to being a structural and functional mimic of rhumAb 4D5, AHNP can also effectively compete with the antibody for binding to the HER2 receptor indicating a similar binding site for the peptide and the parental antibody. To further develop AHNP as an antitumor agent useful for preclinical trials and as a radiopharmaceutical to be used for tumor imaging, a number of derivatives of AHNP have been designed. Structure-fraction relationships have been studied using surface plasmon resonance technology. Some of the AHNP analogues have improved binding properties, solubility, and cytotoxic activity relative to AHNP. Residues in the exocyclic region of AHNP appear to be essential for high-affinity binding. Kinetic and equilibrium analysis of peptide-receptor binding for various AHNP analogues revealed a strong correlation between peptide binding characteristics and their biological activity. For AHNP analogues, dissociation rate constants have been shown to be better indicators of peptide biological activity than receptor-binding affinities. The well-documented antibody effects can be mimicked in tumor therapy by much smaller antibody-based cyclic peptides with potentially significant therapeutic advantages. Strategies used to improve binding properties of rationally designed AHNP analogues are discussed.

Introduction

HER2 (neu, c-erbB2) is a member of the epidermal growth factor (EGFR) or HER family of tyrosine kinase receptors that also includes HER 1 (EGFR, c-erbB 1, HER3 (c-erbB3), and HER4 (c-erbB4). Amplification of HER2 gene and overexpression of HER2 protein has been found in breast and ovarian cancers, as well as tumors of the lung, salivary gland, kidney, and bladder. Greater expression of HER2 on transformed cells than on normal epithelial tissues allows selective targeting of tumor cells using various strategies. See references 1–14 listed below)

Recently, some progress has been made in the development of monoclonal antibody-based therapeutics targeting tumor cell surface antigens (see reference 15 listed below for a recent review). The anti-HER2 antibody "trastuzumab" (Herceptin; Genentech, San Francisco) produces objective responses in some patients with advanced breast cancer showing overexpressed HER2 oncoprotein. The antibody has been shown to antagonize the constitutive growth-signaling properties of the HER2 system, enlist immune cells to attack. and kill the tumor target, and augment chemotherapy-induced cytotoxicity. (See reference 16 below.) Another important application of antibodies that has been extensively developed over the past two decades is tumor imaging by numerous anticancer antibodies against various molecular targets including breast cancer imaging. (See reference 17 below.)

Application of intact antibody molecules as therapeutic or diagnostic molecules remains limited, since they may cause an immune response and have little tumor penetration and high background noise. One of the ways to overcome the limitation of therapeutic macromolecules is to develop a small molecule. A promising approach is to design small peptides derived from the antigen-binding site of antibodies. Historically, few therapeutic peptide products have been used in the clinic because of the difficulties with delivery, stability, and above all, with cost-effective and reliable peptide manufacture. However, recent progress in high quantity peptide synthesis, as well as in screening and optimization of peptide leads, has resulted in an explosion in the number of candidate peptides and a renewed interest in their commercial development. (See reference 18 below.)

Since complementarity-determining regions (CDRs) of antibodies mediate their high affinity binding and specificity to antigens (See reference 19 below), peptide analogues of CDRs can be developed for antibodies with known sequences and structures. (See reference 20–24 below.) The strategy of designing CDR-based mimetics has been widely used in rational drug design. (See references 25–39 below.) Although many of the reported peptides display highly specific antigen binding similar to the parenteral antibody, their antigen-binding affinity is in most cases substantially lower.

Recently, the design of an anti-HER2 peptide mimetic (AHNP, peptide (1), Table 1) derived from the structure of the CDR-H3 loop of the anti-HER2 rhumAb 4D5, and demonstrated its in vitro and in vivo activities in disabling HER2 tyrosine kinases similar to the monoclonal antibody was reported. (See reference 40 below.).

Binding of AHNP has been studies by means of surface plasmon resonance (Biacore) technology. In Biacore experiments, one of the interacting molecules (termed the ligand) is immobilized on the sensor surface, and the other interactant (termed the analyte) is continuously flown over that surface in a micro-flow cell. The interaction between the ligand and the analyte are monitored using a light source that is reflected at the immobilized chip. Binding of the analyte to the immobilized ligand changes the resonance angle of the reflected light due to changes in the refractive index of the surface. The response is plotted in real time in the form of sensorgram curves. The advantage with this approach is its sensitivity, ease of use, and ability to perform experiments with few microgram quantities of proteins and peptides. In addition, the kinetic binding studies reveal association and disassociation rates of the analyte which may be more relevant for understanding the pharmacokinetics of drug-receptor interactions.

Figure 1:
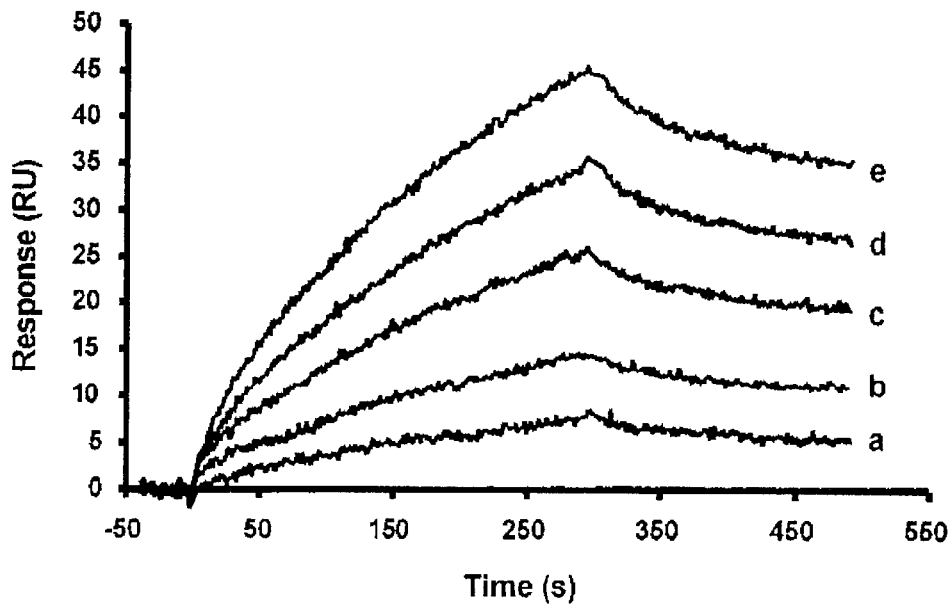
FIG. 1. Biosensor dose dependence curves for binding of AHNP to the immobilized HER2 receptor. AHNP was injected at 0.5 µM (a), 1 µM (b), 2 µM (c), 4 µM (d), and 8 µM (e) concentrations at a flow rate of 20 µL/min. Sensorgrams show binding of AHNP to the immobilized HER2 (first 300 s) followed by the peptide dissociation from the receptor surface (last 240 s).

A typical sensorgram for AHNP binding to the HER2 receptor is shown in FIG. 1. Kinetic constants were estimated by global fitting analysis of the titration curves to the 1:1 Langmurian interaction model, which gave a $^k$on of $1.41\times10^3$ M$^{-1}$s$^-$, and a $^k$off of $4.53\times10^{-4}$ s$^{-1}$. The $^k$off/$^k$on ratio gave a value of 0.32 µM for the dissociation constant ($^K$D). The curves shown in FIG. 1 were calculated from the experimentally observed curves by successive subtractions of signals obtained for the reference surface and averaged signals for the running buffer injected under the same conditions as the tested peptide. (See references 41–44 below.) Good fitting of experimental data to the calculated curves has been observed, suggesting a simple pseudo-first-order interaction between the peptide and the receptor.

A rational design and structure-function analysis of AHNP analogues with improved pharmacological features that could be used as antitumor agents and developed into radiopharmaceuticals is discussed here.

Results

A number of anti-HER2/neu peptide mimetic (AHNP) analogues have been engineered into better therapeutic agents in terms of their binding properties, specificity, and solubility. Ways to incorporate a reactive amino group to conjugate fluorescent and positron emission tomography (PET) agents (see reference 45 below) and studies its effect on binding to the receptor were explored.

Competition Studies

Figure 2:
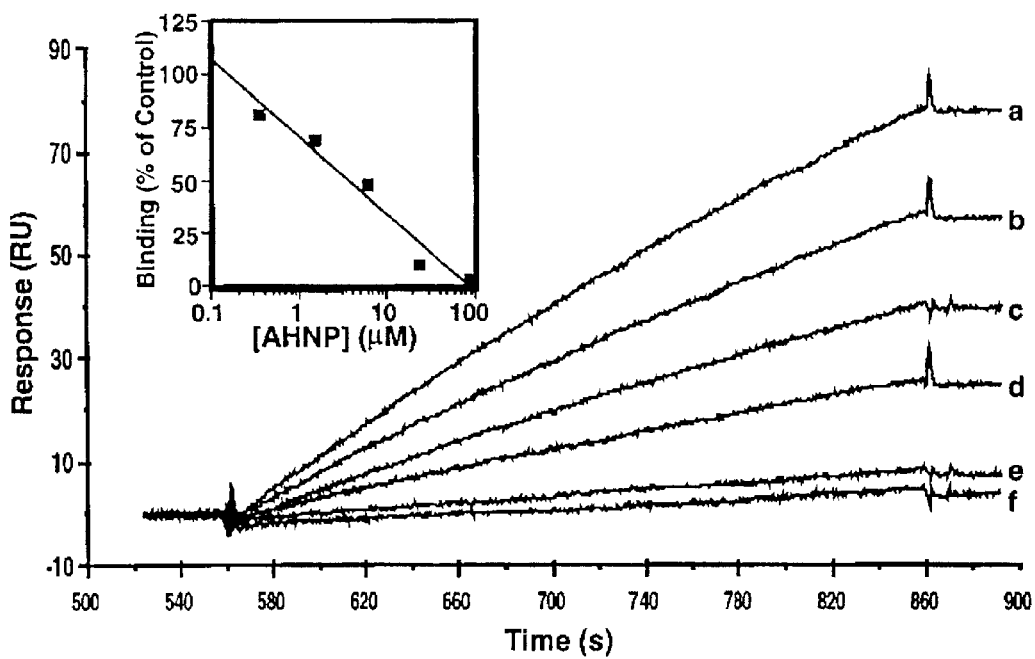
FIG. 2. Biacore analysis of the inhibitory effect of AHNP on rhumAb 4D5 binding to immobilized HER2. Sensorgrams show binding of 1 nM rhumAb 4D5 to HER2 after preinjection of 0 µM (a), 0.35 µM (b), 1.4 µM (c), 5.6 µM (e), and 89 µM (f) AHNP.

It was shown earlier that the AHNP peptide can mimic some functions of the anti-HER2/neu antibody, rhumAb 4135 in vitro and in vivo (see reference 40 below). The structural mimicry of rhumAb 4D5 by AHNP has been analyzed in terms of binding to the HER2 receptor by means of competition binding between studies between AHNP and the parenteral antibody. To that end, injections of AHNP at variable concentrations (from 0 to 90 µM) were followed by injections of rhumAb 4135 at a constant 1 nM concentration, using the "Coinject" mode of the Biacore instrument. Increase in the amount of preinjected AHNP resulted in a steady inhibition of the antibody binding (FIG. 2) with an apparent $IC_{50}$ of 3.4 µM, indicating overlapping binding sites for AHNP and rhumAb 4135 on the surface of HER2.

Design of AHNP Analogues

A number of modifications have been introduced to the sequence of the AHNP peptide to improve its receptor binding and solubility, properties that are important for both major applications: as a therapeutic and as a tumor imaging agent. For the PET studies, $^{18}F$ and $^{90}Y$ will be attached via an α- or ε-amine group of AHNP. (See reference 45 below.) Thus, it is necessary to improve AHNP by either increasing the accessibility of the N-terminal residue or by introducing a Lys residue, which could be readily labeled without diminishing the binding affinity. Two types of changes have been made: (1) addition of polar groups, and (2) mutation of Met to Lys and introduction of D-isomers at the termini. Most of the changes in AHNP were restricted to the N- and C-terminal residues outside the loop constrained by the disulfide bond to preserve the binding nature of AHNP.

Chronologically, peptide 8 was the first AHNP analogue that was designed based on the structures of monoclonal antibodies 4D5 and its rat homologue 7.16. To increase rigidity of the cyclic peptide, peptide 2 was designed in which one of the R-turn forming Gly residue has been deleted. (See reference 40 below.) Three other analogues have been designed to analyze effects of different substitutions on biological activity, binding properties, and solubility. An AHNP peptide has been designed based on the structure of 2 by replacing the C-terminal carboxylate by an amide group. In 3, the N-terminal Phe of the AHNP peptide has been replaced with Tyr, and in 4, aromatic residues positioned before and after the disulfide bond were replaced with the D-amino acid optical isomers. A Lys residue has been included in the sequence of peptide 2 by either replacing Met (resulting in the 6 analog) or by placing it as a C-terminal residue (5).

The designed AHNP analogue peptides have been synthesized, cyclized,(except for peptide 9 used as a control), and tested for binding to HER2, biological activity in an MTT assay, and solubility (Table 1). Binding constants including the association ($^k$on) and dissociation ($^k$off) rate constants, and the equilibrium dissociation constant ($K_D$) shown in Table 1 were determined by analyzing dose dependence curves obtained for each AHNP analogue in a similar fashion as described for AHNP. Effects of different substitutions/additions in AHNP sequence on receptor binding, biological activity, and solubility are summarized in Table 1.

Kinetic Binding Analysis of the AHNP Analogues

Biacore analysis of interactions between AHNP analogues and immobilized HER2 has been performed to test effects of the introduced sequence modifications on the binding affinity and kinetic constants for each peptide. Cyclization is known to be an efficient way of constraining peptides in a binding-competent conformation. Consistent with that, the affinity of cyclic peptide 2 for HER2 was more than 5-fold higher than that of the linear analogue 9 (Table 1). Restriction of the loop by deletion of one of the β-turn glycines (transition from 8 to 2) also resulted in improvements in both affinity and dissociation kinetics. The effect of the charged C-terminal carboxylate group in 2 on binding properties has been tested by replacing it with an amide group in AHNP. Elimination of the charged group in the C-terminal tail resulted in more than 2-fold increase in binding affinity. Similar, but even more dramatic loss of affinity occurred when Lys was introduced as a C-terminal residue in 5 (2.6-fold decrease) and especially when Lys was substituted for Met in 6 (8.8-fold decrease). In the latter case, in addition to the detrimental effect of the C-terminal hydroxyl group, a charge Lys residue replaces a hydrophobic Met residue, which may be important for binding. In contrast, significant improvement in binding (more than 2-fold) has been achieved by introducing a polar hydroxyl group in the N-terminal residue by replacing Phe with Tyr in 3 (Peptide No. 3 in Table 1: SEQ ID NO: 113). This peptide also had the lowest dissociation rate constant ($k_{off}$) among all tested AHNP analogues ($2.94 \times 10^{-4}$ s$^{-1}$), which is comparable with the $k_{off}$ of $1.23 \times 10^{-4}$ s$^{-1}$ observed for rhumAb 4D5.(See reference 40 below.)

Solubility.

Four peptides listed in Table 1, 9, 8, 6, and 4 have been shown to have a much higher solubility than the rest of the tested peptides (Table 1). These peptides could be readily dissolved in the PBS buffer, pH 7.4, at 1 mg/mL concentration without adjustment of pH. Good solubility has also been observed for the linear form of all tested peptides. In contrast, all other tested peptides had a limited solubility at 1 mg/mL.

Biological Activity of the AHNP Analogues.

Biological activity of AHNP analogues has been evaluated by their ability to inhibit cell proliferation using standard 3,(4,5-dimethylthiazol-2-yl)2,5-diphenyl-tet-razolium bromide) (MTT) assays. (See reference 46 below.) HER2-expressing transformed tumor cells (T6–17) were used for this purpose. (See reference 40 below.) In MTT assays, AHNP inhibited the growth of T6–17 cells, overexpressing transformed cell line, dose-dependently at concentrations ranging from 0.01 to 10 µg/mL. Biological activity of AHNP analogues is shown in Table 1. Each value represents an average of at least four samples. Standard error did not exceed 5% for any of the studied analogues. A wide range of activities has been observed for different peptides depending on the nature of introduced modifications. Analogue 3, which has an enhanced receptor-binding affinity (KD=150 nM), was also the most active peptide in the MTT assay, showing almost twice the activity of AHNP (Table 1).

Accessibility of the N-Terminal Amino Group for Labeling.

Since AHNP analogues can selectively bind to the oncogenic HER2 receptor, which is overexpressed in many different forms of cancer, fluorescently or radiolabeled AHNP derivatives could be potentially used as tumor imaging agents. Therefore, one of the goals was to obtain AHNP analogues that could be easily modified. Accessibility of different N-terminal or Lys amino groups for labeling with FITC was estimated by the HPLC analysis of the peptide-FITC reaction mixture as described in Experimental Procedures. The N-terminal amino group of AHNP has a very limited accessibility for fluorescent labeling by FITC (about 2–5% of the theoretically expected yield). To develop AHNP into a radiopharmaceutical, an active AHNP analogue containing a reactive amino group was designed. FITC labeling studies revealed that the N-terminal amino group of AHNP may be inaccessible for labeling. On the basis of the molecular model, it appears that the N-terminal aromatic residue buried in the hydrophobic core (FIG. 3A) may hinder access of the bulky molecule, FITC. To overcome this problem, a more flexible Gly residue was placed at the N-terminus just before Phel (7). However, this also did not significantly improve the degree of labeling (7–10% yield), suggesting that stearic hindrance may still be a factor. Further molecular modeling studies showed that 7 can adopt two main low-energy conformations with different orientations of the N-terminal Gly (FIGS. 4A and 4B). In one of the conformational states, the N-terminus was oriented outside the ring created by the disulfide bond and was therefore solvent-exposed (FIG. 4A). However, in the second confirmation, Gly was oriented toward the inside of the ring and was buried between the ring residues (FIG. 4B). Obviously, the second conformational state may be predominant in solution for 7, which may explain its poor accessibility. Also, since Gly in the second conformational state is positioned very close to the disulfide bond, it is likely to interfere with peptide cyclization. This may account for an unusually slow cyclization rate that has been observed for 7 relative to other analogues. Cyclization half-time for 7 (about 6 days) is about 3-fold longer than a typical half-time, observed for 2 and other analogues. Insertion of Gly inside the ring weakened the hydrophobic core leading to an increased solubility of 7 (Table 1). As expected, both Lys-containing peptides, 6 and 5, were completely accessible for labeling showing almost qualitative reactivity of their E-amino groups with FITC. Preliminary binding data obtained with FITC-modified 5 indicate that it has a receptor-binding affinity similar to the unlabeled peptide 5.

In vivo Clearance and Imaging.

AHNP (Peptide 3 in Table 1: SEQ ID NO: 113) labeled with $^{99m}$Tc was used to estimate the blood clearance in nude mice. The mean half-life of AHNP in the blood is about 50 minutes, and the peptide is completely cleared by about 5 hrs. (FIG. 7). This suggests that AHNP is useful for imaging purposes.

Mice bearing T6–17 xenografted tumors received purified $^{99m}$Tc-labeled AHNP. In a preliminary analysis, the $^{99m}$Tc labeled AHNP preferentially accumulated to the tumor compared to the normal tissue, and the ratio of the % i.d./g is over 3-fold greater on the tumor (see FIG. 8 and Table 2) than on normal tissue, suggesting that these molecules can be engineered for tumor detection.

Enhanced Tumor Cell Growth Inhibition with ANHP and Tamoxifen.

AHNP has previously been demonstrated to enhance growth inhibition of T6-17 tumor cells in vitro and in vivo in combination with chemotherapeutic agent doxirubicin (Park et al., *Nature Biotechnology*; 18: 194–198 (2000)). Similar to those results, it was demonstrated that ANHP (YCDGFYACYMDV-SEQ ID NO: 113) in combination with tamoxifen enhanced growth inhibition of parental MCF-7 p185-expressing and MCF-7/H2 p185-overexpressing cells (FIG. 9).

Discussion

Surface plasmon resonance analysis was the method of choice for characterization of peptide-receptor binding, since there was interest in not only equilibrium data, but also kinetic parameters of the interactions. Because of the large number of tested peptides, the only practical way for screening was immobilization of HER2 on the chip and injection of peptides as soluble analytes. Although direct detection of analytes smaller than 5000 Da was once considered unfeasible with standard Biacore protocols (see references 47 and 48 below), recent advances in the technology, such as higher sensitivity and improved microbluidics, have enabled development of direct binding assays between immobilized proteins and low-molecular-weight analytes including peptides (see references 44 and 49–51 below) and organic compounds (see references 52–58 below). Reproducible data with a high signal-to-noise ratio have been reported even though the change in molecular mass upon analyte binding was in some cases as low as 1%. (see references 55 and 58 below). In some instances, modifying experimental conditions by using very dense ligand surfaces and/or high peptide concentrations with high flow rates was critical for obtaining good signal-to-noise rations (see references 55 and 58 below). Accuracy of experiments with low signal levels can be improved by increasing the number of collected data points, increasing analyte concentration, and signal averaging of data derived from repeat sensorgrams. (see reference 44 below). In Biacore studies of low-molecular-weight-cyclic peptides, highly reproducible signals could be obtained after double corrections of data for the reference surface and the running buffer signals.

A large number of antibody-derived peptides have been reported, yet remarkably few of them have been demonstrated to mimic the parental mAb in terms of structure and function. The data show that AHNP not only induce antitumor effects such as its parent antibody, but also share binding epitope on the HER2 receptor. This information is very important, since peptides are usually designed to mimic antigen-binding properties and therapeutic effects of corresponding mAbs. Although peptide mimetics that bind to receptors are often presumed to be direct structural analogues of the loops that they mimic, and are therefore expected to have the same binding sites as the loops, this is not always an obvious fact and has to be proven experimentally. It has been shown that some peptide mimetics designed to mimic enzyme substrates and even some natural enzyme inhibitors do not bind in a substrate-like manner. (See references 59–63 below.) For a large number of receptors, analysis of the endogenous peptide and antagonists' binding sites by site-directed mutagenesis indicated that antagonists and the parent peptide bind to different subsites.(See references 64-66 below.) Backward binding is a common occurrence which has been exploited to develop novel inhibitors. (See references 59, 60 and 67 below.)

Although it is shown that AHNP and rhumAb 4D5 interact with the same binding site on the HER2 surface, it appears that the nature of receptor interaction with the peptide and the antibody are quite different. Analysis of surface regeneration conditions that are efficient (or necessary) for the destruction of a ligand-analyte complex can help provide insight into the major forces involved in the complex formation. In the rhumAb 4D5-HER2 complex, electrostatic interactions seem to play a predominant role, since the antibody could be easily washed off the receptor surface by high salt concentrations (4.5 M $MgCl_2$), but was resistant to treatment with either detergent (0.2% SDS) or a mixture of organic solvents. In contrast, the AHNP-HER2 complex was resistant to salt, but readily dissociated upon addition of either detergent or organic solvents, suggesting the involvement of hydrophobic interactions in complex stability. Obviously, aromatic residues at both sides of the disulfide bond, as well as the hydrophobic residues in the tail of AHNP and its analogues contribute significantly to the overall energy of binding, since substitution or modification of these residues adversely affects the binding affinity (Table 1). Moreover, it is clear that for the AHNP peptide, in addition to the binding forces inherited from the CDR3 loop of rhumAb 4D5, which obviously direct the peptide to bind to the CDR3 epitope on the receptor surface, some new complex-stabilizing hydrophobic bonds are formed between the peptide and receptor, which are absent in the parent antibody.

Poor solubility of peptidomimetics often limits their usefulness as therapeutic agents. The solubility of some AHNP analogues was improved without further loss of the binding characteristics. Molecular modeling was used to understand the effect: of mutations on solubility. Molecular modeling AHNP showed formation of a hydrophobic core by Phe 1, Cys2, Phe5, Ala7, Cys8, Tyr9, and Met10 residues upon peptide cyclization (FIG. 3A). Increasing backbone flexibility by adding one more Gly residue (8) enhanced spatial separation and mobility of the hydrophobic residues which may have resulted in the improved solubility. Replacement of Met 10 within the improves solubility by reducing the size of the hydrophobic core (FIG. 3B). Phe 1 and Tyr9 at the termini of AHNP form the center of the core. Replacement of these residues by their D-isomers increases the separation between them by changing the orientation of the aromatic side chains relative to each other (FIG. 5), which leads to the increased solubility. Interestingly, when polar groups were introduced in residues outside the hydrophobic core (in 2 and 5), no improvement in solubility has been observed (Table 1), confirming a critical role played by the hydrophobic core in peptide solubility. Another analogue that displayed a good solubility is 7.

Balancing hydrophilicity and hydrophobicity is critical for high affinity binding, especially for small molecules. In this study, the effects of different sequence modifications was tested in the AHNP analogues on their biological activity and binding; properties. Interestingly, the C-terminal tail region of the studied peptides was fount to play an important role in receptor binding. In antigen-antibody complexes, the CDR loops and framework regions immediately after the CDR loops have been reported to be critical for antigen binding. (See references 36, 37, 68 and 69) However, it is not clear how residues from the framework proximal to CDR can play a critical role in binding.

The C-Terminal Met, Asp, and Val residues in AHNP analogues; are derived from the framework region of anti-HER2 antibodies. Replacement of the Met residue in the tail with Lys (6) resulted in a dramatic decrease in binding affinity by about 1 order of magnitude (Table 1). The effect of addition of a Lys residue following the tail sequence 5 on receptor binding affinity was less dramatic but also significant (2.5-fold decrease, Table 1). Molecular modeling of the AHNP peptide revealed that the Met residue and aromatic residues form a hydrophobic core (FIG. 3A). This formation of the hydrophobic core may be critical for receptor binding, having either enthalpic (formation of hydrophobic bonds with receptor residues) or entropic (constraining the peptide in an active conformation) effects, or both. The Met residue is a part of the core and may also be important for its integrity, which is consistent with the observed improvement in aqueous solubility of 6 relative to 2 (Table 1). These observations suggest that additional interactions of the C-terminal tail residues of the AHNP analogues with the receptor may be partly compensating for the diminished interface area in the peptide-receptor complex relative to the antibody-receptor complex.

Structure-activity relationship has been studied for the whole series of peptides. Cell growth inhibition activities obtained in the MTT assays for each analogue were plotted versus their affinity for HER2, estimated in the surface plasmon resonance study (;FIG. 6A). A strong correlation ($r^2$=0.89) has been determined between the peptides' receptor affinities and their inhibitory effects, suggesting that the observed biological activities are mediated by binding to HER2. As expected, the most active peptide (3) had the highest binding affinity, while the affinity of the least active (6) was the lowest among all analogues. Although the overall correlation was rather strong, some notable deviations from the straight line have been observed. Thus 2 and 7 peptides have a relatively small (12%) difference in affinities, but much more pronounced difference (41%) in inhibition. Similar discrepancies have been detected by comparing AHNP with 4 (9% difference in affinity versus 35% difference in inhibitory effect). The biggest inconsistency has been observed for the 7 and 5 pair. Although 5 is 27% more active, it binds to the receptor with a 14% lower affinity than 7 (Table 1).

To test whether these discrepancies could be explained by differences in the kinetic rate constants, activity data were plotted against the dissociation rate constants ($k_{off}$) observed in Biacore assays (FIG. 6B). Remarkably, inhibitory activity showed an even stronger correlation with the $k_{off}$ ($r^2$+0.94), than with the $K_D$. Comparison of the two plots (FIGS. 6A and 6B) suggests that stronger inhibitory activity observed for AHNP, 2, and 5 can be better explained by their slow dissociation rates rather than by their high receptor-binding affinities.

Analysis of the drug-receptor dissociation rate is essential for a proper design and interpretation of receptor-binding studies, as well as for the selection of drug candidates. (See reference 70 and 71 below). For slowly dissociating drugs binding equilibrium cannot be reached in short-incubation time experiments, thus prevent competitive inhibition. A slow dissociation rate has been shown to play an important role for the biological activity of the drug. (See references 55 and 70.) Since rapidly dissociating drugs can reach a competitive binding equilibrium with the endogenous receptor ligands, they are easily displaced from the receptor sites by increased concentrations of the ligands, which in most cases have higher receptor-dinging affinities than the drugs. However, slowly dissociating drugs form inactive receptor-drug complexes which have very long half-lives. Even if the overall binding affinity is low because of a slow association rate, these drugs can provoke a permanent receptor blockade, which cannot be displaced by the endogenous ligands, thus acting as almost nonreversible antagonists. Dissociation rate might play an important role in long-term effects of drugs. (See reference 70 below). Therefore, analysis based in $K_D$ values alone, could overlook potentially strong inhibitors that have slow binding and slow dissociation rates. (See reference 72 below). Data demonstrates rhumAb 4D5 has about 2 orders of magnitude higher receptor-binding affinity than the AHNP peptides (Table 1). However, this difference is mostly due to a faster on-rate (higher $k_{on}$) of the antibody. In terms of the dissociation rate constant $k_{off}$, receptor-binding properties of the optimized peptides are very similar to those of the antibody. Although a big excess of AHNP is required to inhibit rhumAb 4D5-HER2 interaction (because of the difference in the binding affinity), the optimized peptides and the antibody have comparable biological activities in the MTT assay, in line with the observation that $k_{off}$, rather $K_D$, determines the biological activity of the AHNP peptides.

Data shows the importance of the dissociation rate constant for biological activity of AHNP analogues. For this series of peptides, $k_{off}$ has been shown to have a higher predictive value for the expected inhibitory effects than the dissociation constant ($K_D$) traditionally used for these purposes. Since AHNP analogues produce their biological effects by binding to HER2 and possibly inducing a conformational charge that deactivates the receptor, the data indicate that increasing the half-life of the inactive peptide-receptor complexes is more efficient for the inhibition of normal receptor functioning than increasing the equilibrium concentration of these complexes.

In the HER2 receptor system, AHNP peptides compete with some fast-occurring processes (either binding or conformational rearrangements) that lead to receptor signaling. Because of their rapid rate, these processes might reoccur each time immediately after the peptide dissociates from the receptor surface and before it can rebind. By remaining on the receptor surface for prolonged periods of time, AHNP analogues with low dissociation rates effectively block receptor activity. The data suggest that high binding affinity does not necessarily have to be the main goal that determines the success of structure-based drug design. As shown for the AHNP mimetics, the dissociation rate constant can be a very important constituent of peptides; biological activity. Depending on a drug's mechanism of action, a slow $k_{off}$ can compensate for low affinity in certain situations.

Results from blood clearance analysis of $^{99m}$Tc-labeled AHNP suggested a use for this mimetic for in vivo imaging assays. Subsequent assays in nude mice xenografted with p185-expressing tumors (T6–17 fibroblast-derived line) showed that AERP preferentially accumulated to the tumor compared to normal tissue (FIGS. 8A–8B). Some accumulation in liver and kidney was also observed. Nevertheless, these studies suggest that AHNP can be engineered as a useful imaging agent. Further refinements of AHNP are in progress.

Lastly, similar to what was observed for AHNP administered in combination with doxirubicin, a combination of an AHNP analogue (SEQ ID NO: 143) and tamoxifen enhanced in vitro inhibition of proliferation of p185-expressing and -overexpressing MCF/7 breast carcinoma cells.

In summary, for a number of AHNP analogues, significant improvements in receptor-binding affinity, solubility, or accessibility for labeling was achieved by introducing additional hydrophobic or polar groups. More importantly, the optimized analogues showed almost antibody-like dissociation rate constant, which, as shown in structure-activity studies, is a critical activity-determining parameter for this class of peptides. Optimization of both entropic and enthalpic components of peptide-receptor binding, performed in this study, has significantly improved solubility and binding properties of antibody-derived peptides (including affinities and dissociation rate constants) while retaining the high specificity typical for a full-size antibody. These analogues were demonstrated to be useful for in vitro growth inhibition of p185-expressing tumor cell lines, and in vivo imaging of xenotransplanted p185-expressing tumor tissue.

Experimental Section
Peptide Synthesis and Cyclization

Linear peptides (95% purity) were ordered from the Protein Chemistry Laboratory, University of Pennsylvania. Peptides purity and identity was confirmed by reverse phase high performance liquid chromatography (RP HPLC) and MALDI mass spectrometry, using a time-of-flight mass spectrometer (Micromass TofSpec; Micromass Inc., Beverly, Mass.). The peptides were cyclized by air oxidation in distilled water adjusted to pH 8.0 with $(NH_4)_2CO_3$ at 0.1 mg/mL and 4° C. Progress of the oxidation was controlled by measuring amounts of free thiols with 5.5°-dithiobis(2-nitrobenzoic) acid (DTNB). Briefly, 0.4 mL of an AHNP peptide (0.1 mg/mL) and 5 µL of DTNB (20 mM) were added to 0.2 mL of 0.1 M sodium phosphate buffer, pH 8.0. Absorbance at 412 nm was measured. an compared with the linear unoxidized peptides. The cyclized peptides were lyophilized and their purity was analyzed by RP HPLC using a C18 semipreparative column (Waters, Milford, Mass.). Typically, purity of higher than 95% was obtained for the cyclized peptides. Aliquotes of 1 mM stock solutions have been prepared for each peptide and kept at −20° C. to be thawed prior to the binding or bioassay studies. Peptide concentrations were confirmed by UV spectrophotometry using extinction coefficients at 280 nm calculated for each peptide as described in reference 73.

Interaction Studies.

Binding experiments were performed with the surface plasmon resonance based biosensor instrument Biacore 3000 (Biacore AB, Uppsala, Sweden) at 25° C. Recombinant purified HER2 receptor composed of the ectodomain of HER2 fused to the Fe of human IgG was provided by Dr. Che Law, Xcyte Therapeutics, Seattle, Wash. Immobilization of HER2 in the sensor surface was performed following the standard amine coupling procedure according to manufacturer's instructions. Briefly, 35 µL of a solution containing 0.2M N-ethyl-N-(dimethylaminopropyl) carbodiimide (EDC) and 0.05 M N-hydroxysuccinimide (NHS) were injected at a flow rate of 5 µL/min to activate carboxyl groups on the sensor chip surface. HER2 (40 ng/mL in 10 mM NaOAc buffer, pH 5.0) was flowed over the chip surface at a flow rate of 20 µL/min until the desired level bound protein was reached. Unreacted protein was washed out and unreacted activated groups were blocked by the injection of 35 µL of 1 M ethanolamine at 5 µL/min. The final immobilization response of HER2 was 3500 RU. A reference surface was generated simultaneously under the same conditions but without HER2 injection and used as a blank to correct for instrument and buffer artifacts. Peptides were injected at variable concentrations at 20 µL/min flow rate and binding to the HER2 receptor immobilized on the chip was monitored in real time. Each sensorgram consists of an association phase (first 240 s), reflecting binding of the injected peptide to the receptor, followed by a dissociation phase (300 s), during which the running buffer is passed over the chip and the bound peptide is being washed off the receptor surface. In competition studies, peptides were pre-injected for 5 min at 20 mL/min at concentrations ranging from 0 to 90 µM. rhumAb 4D5 (Genentech) was then injected for 5 min at 1 nM concentration in the "Co-inject" mode. A control cyclic peptide CD4-M was used in some studies and was shown to be no different than blank control.

FITC-Labeling of Peptides.

Two milligrams of each peptide were dissolved in 1 mL of 0.02 M $Na_2CO_3$ $NaHCO_3$ buffer, pH 9.1, containing 0.02 M NaCl. A total of 0.5 mL of 1% (w/v) fluorescein 5-isothiocyanate (FITC) dissolved in methanol was added to the peptide solution, and the reaction mixture was incubated in the dark for 2 h at room temperature. The reaction was terminated by rapid passage of the reaction mixture through a Sephadex G-10 column equilibrated with isotonic phosphate-buffered saline, pH 7.4, and further purified by C18 reverse-phase HPLC. The purified FITC-labeled peptides were dried under vacuum. Peptide identity was confirmed by MALDI mass spectroscopy.

MTT Assay.

The MTT assay has been used for measuring cell growth as previously described in ref 446. Briefly, T6–17 cells were seeded in 96-well plates overnight in DMEM containing 10% FBS (1000 per well). T6–17 is derived from NIH3T3 by overexpressing the human HER2 receptor. Cells were cultured in 100 µL of fresh medium containing 1 µg/mL of peptides for 48 h. This incubation time was optimal for measuring inhibitory effects of different analogues. No improvements in the inhibitory activity could be achieved by increasing the incubation period. A total of 25 µL of MTT solution (5 mg/mL in PBS) was added to each well, and after 2 h of incubation at 37° C., 100 µL of the extraction buffer (20% w/v of SDS, 50% N,N-dimethyl formamide, pH 4.7)

were added. After an overnight incubation at 37° C., the optical density at 600 rim was measured using an ELISA reader.

Molecular Modeling.

Molecular modeling of AHNP has been performed as described previously. Other AHNP analogues were designed by comparative modeling using AHNP as a template. To that end, point mutations or deletions have been introduced in the AHNP sequence using the "Protein Design" application of program QUANTA (Molecular Simulation, MA). Each analogue has been evaluated for the backbone and side chain orientation and solvent effects using a combination of energy minimization (CHARMM) and molecular dynamics simulations at room temperature (300'K) and at 600'K. Low energy conformers were further minimized and compared with AHNP and the native conformation of the template CDR3 loop of rhumAb 4D5.

Radiolabeling and Chemistry

For the radiolabeling of the AHNP with $^{99m}$Tc, diethylenetriamine pentaacetate (DTPA) was used as the chelating agent. Since the complexation constant of $^{99m}$Tc-DTPA is moderate, 6-Hydrazinopyridine-3-carboxylic acid (HYNIC) and tricine can be used for $^{99m}$Tc complexation.

HYNIC synthesis: the preparation of 6-hydrazinopyridine-3-carboxylic acid (HYNIC) is going to be carried out in a similar methods reported by Abrams et. al. [74].

Conjugation of HYNIC to AHNP: The conjugation of HYNIC to AHNP was performed in a conventional way. Briefly, To a solution of AHNP (1 mg AHNP dissolved in 1 mL 0.1 M pH 8.0 HEPES buffer) was added a fresh 20 mg/mL solution of SHNH in dry DMF dropwise with agitation (5:1 molar ratio of SHNH/peptide). The volume of DMF added was less than 10% of the total volume. The reaction mixture was incubated at room temperature for 30–60 min, and then purified by semi-preparative RP HPLC. The collection was dried by rotary evaporation and lyophilized. The molecular weight of the coupled peptide was determined by ESI-MS.

$^{99m}$Tc labeling of AHNP: 10 μL (about 1 μg) of conjugated peptide in water, 50 μL pH 5.2 0.25 M ammonium acetate, 10 to about 100 μL (1–10 mCi) of $^{99m}$Tc-pertechnetate, 15 μL of a 100 μg/μL Tricine water solution will be mixed together. To the mixture will be added 4–8 μg $SnCl_2$ in 10 μL 0.01 N HCl. After incubation at room temperature for 30–60 min, the labeled peptide will be analyzed by reversed-phase (RP) HPLC, with water/acetonitrile containing 0.1% TFA as mobile phase, and purified by size-exclusion (SE) HPLC with 0.1 M pH 7.2 phosphate buffer as mobile phase and fractionating. The fraction with the highest radioactivity would be used for in vitro and in vivo tests.

DTPA Chelation

Briefly, 1 mg of AHNP in 1 mL pH 8.0 to about 8.5 0.25 M bicarbonate buffer, a suspension of the cyclic DTPA anhydride in 50 μL DMF will be mixed with agitation. The final DTPA/peptide molar ratio was about 5 to about 10:1. After 30 min incubation at room temperature, the coupled peptide will be purified by semi-preparative RP HPLC with water/acetonitrile containing 0.1% TFA as mobile phase. The collection was dried by rotary evaporation and lyophilyzation. The molecular weight of the coupled peptide was determined by ESI-MS.

$^{99m}$Tc labeling: The DTPA-conjugated peptide was labeled with $^{99m}$Tc in neutral medium. 1 to about 5 μg (10 to about 50 μL) of the DTPA-HNERm solution was mixed with 10 μL (1 to about 10 mCi) of pertechnetae and 10 μL 4 to about 8 μg $SnCl_2$ in 0.01 N HCl. After incubation at room temperature for 30 min, the radiolabel was analyzed by RP HPLC with water/acetonitrile containing 0.1% TFA as mobile phase, and purified by SE HPLC with 0.1 M pH 7.2 phosphate buffer as mobile phase and fractionating. The fraction with highest radioactivity was used for in vitro and in vivo tests.

DOTA Chelation

DOTA is commercial available. It was activated by NHS and ECD first and then coupled to AHNP. The procedure of coupling is based on the work of Lewis et al. [75]. Briefly, Activated DOTA was prepared (4° C., 45 min) using DOTA, sodium bicarbonate, sulfo-NHS, and EDC at 10:30:10:1 molar ratios. Conjugation was carried out by adding a 30-90-fold molar excess of activated DOTA to AHNP, adjusting pH to 8, and incubating for overnight h at 4° C. Purification was achieved by RP HPLC with water/acetonitrile containing 0.1% TFA as mobile phase. The collection was dried by rotary evaporation and lyophilysation. The molecular weight of the conjugate was determined by ESI-MS.

$^{99m}$Tc labeling was performed as described above for DOTA chelation.

Blood Clearance.

AHNP labeled with $^{99m}$Tc was used to estimate the blood clearance in nude mice. Each animal of four groups received 5 μCi of the radioactivity through i.v. injection. After a given time post injection, the animals were anesthesized and their blood was collected via retro-orbital sinus. The radioactivity in the blood samples, expressed as percentage injection dose per gram of the blood sample (% i.d./g, n=3+SE), was plotted against the time intervals between the injection of the radioactivity and the collection of the blood samples.

Animal Tumor Imaging and Biodistribution of AHNP.

NCr homozygous athymic (nude) mice were purchased from the National Cancer Institute (Bethesda, Md.). An aliquot of $2 \times 10^6$ T6–17 tumor cells (NIH 3T3 cells stably transfected with p185$^{HER2/neu}$) were suspended in 200 ul of PBS and injected subdermally. Six days after tumor xenograft, tumors reached about 200–230 mm$^3$ in volume. Mice bearing T6–17 xenografted tumors received purified $^{99m}$Tc labeled AHNP. The imaging was taken 30 minutes and 90 minutes postinjection and biodistributions were carried out after the imaging was finished (Table 2).

Combination Treatment.

Both MCF-7 parental strain (MCF/Par) and HER-2-overexpressing (MCF-7/H2) tumor-cells were treated with tamoxifen alone (TAM); with ANHP analog FCGDGFYACYMDV (SEQ ID NO: 143) alone (1 μg/ml); with AHNP analog YCDGFYACYMDV (SEQ ID NO: 113) alone (1 μg/ml); with tamoxifen and the former (SEQ ID NO: 143); and with tamoxifen and the latter (SEQ ID NO: 113) (FIG. 9).

REFERENCES

Each of the following references is incorporated herein in its entirety.

(1) Dougall, W. C.; Qian, X.; Peterson, N. C.; Miller M. J.; Samanta, A.; et al. The neu-oncogene: signal transduction (1) pathways, transformation mechanisms and evolving therapies. *Oncogene* 1994, 9, 2109–2123.

(2) Hynes, N. E.; Stern, D. F. The biology of ebb-2/neu/HER-2 and its role in cancer. *Biochim. Biophys. Acta* 1994, 1198, 165–184.

(3) Reese, D. M.; Slamon, D. J. HER-2/neu signal transduction in human breast and ovarian cancer. *Stem Cells* 1997, 15, 1–8.

(4) Alroy, I.; Yarden, Y. The Ebb signaling network in embryogenesis and oncogenesis: signal diversification through combinatorial ligand-receptor interactions. *FEBS Lett.* 1997, 410, 83–86.

(5) Klapper, L. N.; Kirschbaum, M. H.; Sela, M.; Yarden, Y. Biochemical and clinical implication of the Ebb/HER signaling network of growth factor receptors. *Adv. Cancer Res.* 2000, 77, 25–79.

(6) Drebin, J. A.; Link, V. C.; Greene, M.1. Monoclonal antibodies reactive with distinct domains of the neu oncogene-encoded p185 molecule exert synergistic antitumor effects in vivo. *Oncogene* 1988, 2, 273–277.

(7) O'Rourke, D. M.; Greene, M. I. Immunologic approaches to inhibiting cell-surface-residing oncoproteins in human tumors. *Immunol. Res.* 1998, 17, 179–189.

(8) Murali, R.; Greene, M. I. Structure-based design of immunologically active therapeutic peptides. *Immunol. Res.* 1998, 17, 163–169.

(9) O'Rourke, D. M.; Nute, E. J.; Davis, J. G.; Wu, C.; Lee, A. et al. Inhibition of a naturally occurring EGFR oncoprotein by the p185neu ectodomain: implications for subdomain contributions to receptor assembly. *Oncogene* 1998, 16, 1197–1207.

(10) O'Rourke, D. M.; Kao, G. D.; Singh, N.; Park, B. W.; Muschel, R. J.; et al. Conversion of a radioresistant phenotype to a more sensitive one by disabling ebb receptor signaling in human cancer cells. *Proc. Natl. Acad. Sci. USA*. 1998, 95, 10842–10847.

(11) Zhang, H.; Wang, Q.; Montone, K. T.; Peavey, J. E.; Drebin, J. A.; et al. Shared antigenic epitopes and pathobiological functions of anti-p185(her2/neu) monoclonal antibodies. Exp. *Mol. Pathol.* 1999, 67,15–25.

(12) Wels, W.; Harwerth, I. M.; Mueller, M.; Groner, B.; Hynes, N. E. Selective inhibition of tumor cell growth by a recombinant single-chain antibody-toxin specific: for the ebb-2 receptor. *Cancer Res.* 1992, 52, 6310–6317.

(13) Wels, W.; Harwerth, I. M.; Hynes, N. E.; Groner, B. Diminution of antibodies directed against tumor cell surface epitopes: a single chain Fv fusion molecule specifically recognizes the extracellular domain of the c-ebb-2 receptor. *J. Steroid Bio-them. Mol.* 1992, 43, 1–7.

(14) Xu, F. J.; Boyer, C. M.; Bae, D. S.; Wu, S.; Greenwald, M.; et al. The tyrosine kinase activity of the C-ebb-2 gene product (p185) is required for growth inhibition by anti-p185-ricin-A chain immunotoxin. *Int. J. Cancer* 1994, 59, 242–247.

(15) Weiner, L. M. An overview of monoclonal antibody therapy of cancer. *Semin. Oncol.* 1999, 26, 41–50.

(16) Sliwkowski, M. X.; Lofgren, J. A.; Lewis, J. A.; Hotaling, T. E.; Fendly, B. M.; et al. Nonclinical studies addressing the mechanism of action of trastuzumab (Herceptin). *Semin. Oncol.* 1999, 26, 60–70.

(17) Goldenberg, D. M.; Nabi, H. A. Breast cancer imaging with radiolabeled antibodies. *Semin. Nuclear Med.* 1999, 29, 41–48.

(18) Latham, P. W. Therapeutic peptides revisited. *Nat. Biotechnol.* 1999, 17, 755–757.

(19) Amit, A. G.; Mariuzza, R. A.; Phillips, S. E.; Poljak, R. J. Three-dimensional structure of an antigen-antibody complex at 2.8 A resolution. *Science* 1986, 233, 747–753.

(20) Bruck, C.; Co, M. S.; Slaoui, M.; Gaulton, G. N.; Smith, T.; et al. Nucleic acid sequence of an internal image-bearing monoclonal anti-idiotype and its comparison to the sequence of the external antigen. *Proc. Natl. Acad. Sci. U.S.A.* 1986, 83, 6.578–6582.

(21) Williams, W. V.; Moss, D. A.; Kieber-Emmons, T.; Cohen, J. A.; Myers, J. N.; et al. Development of biologically active peptides based on antibody structure [published erratum appears in *Proc. Natl. Acad. Sci. U.S.A.* October 1989; 86 (20), 8044]. *Prod. Natl. Acad. Sci. U.S.A.* 1989, 86,5537–5541.

(22) Williams, W. V.; Kieber-Emmons, T.; VonFeldt, J.; Greene, M I. L; Weiner, D. B. Design of bioactive peptides based on antibody hypervariable region structures. Development of conformationally constrained and dimeric peptides with enhanced affinity. *J Biol. Chem.* 1991, 266, 5182–5190.

(23) Dougall, W. C.; Peterson, N. C.; Greene, M. I. Antibody-structure-based design of pharmacological agents. *Trends Biotechnol.* 1994, 12, 372–379.

(24) Saragovi, H. U.; Fitzpatrick, D.; Raktabutr, A.; Nakanishi, H.; Kahn, M.; et al. Design and synthesis of mimetic from an antibody complementarity-determining region. *Science* 1991, 253, 792–795.

(25) Takahashi, M.; Ueno, A.; Uda, T.; Mihara, H. Design of novel porphyrin-binding peptides based on antibody CDR. *Bioorg. Med. Chem. Lett.* 1998, 8, 2023–2026.

(26) Takahashi, M.; Ohgitani, Y.; Ueno, A.; Mihara, H. Design of peptides derived from anti-IgE antibody for allergic treatment. *Bioorg. Med. Chem. Lett.* 1999, 9, 2185–2188.

(27) Feng, Y.; Chung, D.; Garrard, L.; McEnroe, G.; Lim, D.; et al. Peptides derived from the complementarity-determining regions of anti Mac-1 antibodies block intercellular adhesion molecule-1 interaction with Mac-1. *J. Biol. Chem.* 1998, 273, 5625-5630.

(28) Avrameas, A.; Temynck, T.; Nato, F.; Buttin, G.; Avrameas, S. Polyreactive anti-DNA monoclonal antibodies and a derived peptide as vectors for the intracytoplasmic and intranuclear translocation of macromolecules. *Proc. Natl. Acad. Sci. U.S.A.* 1998, 95, 5601–5606.

(29) Chatterjee, S. K.; Tripathi, P. K.; Chakraborty, M.; Yannelli, J.; Wang, H.; et al. Molecular mimicry of carcinoembryonic antigen by peptides derived from the structure of an anti-idiotype antibody. *Cancer Res.* 1998, 58, 1217–1224.

(30) Deng, Y.; Notkins, A. L. Molecular determinants of polyreactive antibody binding: HCDR3 and cyclic peptides. *Clin. Exp. Immunol.* 2000, 119, 69–76.

(31) Jouanne, C.; Avrameas, S.; Payelle-Brogard, B. A peptide derived from a polyreactive monoclonal anti-DNA natural antibody can modulate lupus development in (NZBxNZW)Fl mice. *Immunology* 1999,96,333–339.

(32) Sivolapenko, G. B.; Douli, B.; Pectasides, D.; Skarlos, D.; Siiurmalis, G.; et al. Breast cancer imaging with radiolabeled peptide from complementarity-determining region of antitumor antibody. *Lancet* 1995, 346, 1662–1666.

(33) Hussain, R.; Courtenay-Luck, N. S.; Siligardi, G. Structure-function correlation and biostabitlity of antibody CDR-derived peptides as tumor imaging agents. *Biomed. Pept. Proteins Nucleic Acids* 1996, 2, 67–70.

(34) Monnet, C.; Laune, D.; Laroche-Traineau, J.; Biard-Piechaczyk:, M.; Briant, L.; et al. Synthetic peptides derived from the variable regions of an anti-CD4 monoclonal antibody bind to CD4 and inhibit HIV-1 promoter activation in virus-infected cells. *J. Biol. Chem.* 1999, 274, 3789–3796.

(35) Waisman, A.; Ruiz, P. J.; Israeli, E.; Eilat, E.; Konen-Waisman, S.; et al. Modulation of murine systemic lupus erythematosus with peptides based on complementarity determining regions of pathogenic anti-DNA monoclonal antibody. *Proc. Natl. Acad. Sci. U.S.A.* 1997,94, 4620–4625.

(36) Laurie, D.; Molina, F.; Ferrieres, G.; Mani, J. C.; Cohen, P.; et al. Systematic exploration of the antigen binding activity of synthetic peptides isolated from the variable regions of immunoglobulins. *J. Biol. Chem.* 1997, 272, 30937–30944.

(37) Igarashi, K.; Asai, K.; Kaneda, M.; Umeda, M.; Inoue, K. Specific binding of a synthetic peptide derived from an antibody complementarity determining region to phosphatidylserine. *J. Biochem. (Tokyo)* 1995, 117, 452–457.

(38) Brosh, N.; Dayan, M.; Fridkin, M.; Mozes, E. A peptide based on the CDR3 of an anti-DNA antibody of experimental SLE origin is also a dominant T-cell epitope in (NZBXNZW)FI lupus-prone mice. *Immunol. Lett.* 2000, 72, 61–68.

(39) Brash N.; Eilat, E.; Zinger, H.; Mozes, E. Characterization and role in experimental systemic lupus erythematosus of T-cell lines specific to peptides based on complementarity-determining region-1 and complementarity-determining region-3 of a pathogenic anti-DNA monoclonal antibody. *Immunology* 2000, 99, 257–265.

(40) Park, B. W.; Zhang, H. T.; Wu, C.; Berezov, A.; Zhang, X.; et al. Rationally designed anti-HER2/neu peptide mimetic disables PI 85HER2/neu tyrosine kinases in vitro and in vivo. *Nat. Biotechnol.* 2000, 18, 194–198.

(41) Myszka, D. G. Improving biosensor analysis. *J. Mol. Recognit.* 1999, 12, 279–284.

(42) Myszka, D. G.; Jonsen, M. D.; Graves, B. J. Equilibrium analysis of high affinity interactions using BIACORE. *Anal. Biochem.* 1998, 265, 326–330.

(43) Canziani, G.; Zhang, W.; Cities, D.; Rux, A.; Willis, S.; et al. Exploring biomolecular recognition using optical biosensors. *Methods* 1999, 19, 253–269.

(44) Ober, R. J.; Ward, E. S. The influence of signal noise on the accuracy of kinetic constants measured by surface plasmon resonance experiments. *Anal. Biochem.* 1999, 273, 49–59.

(45) Downer, J. B.; McCarthy, T. J.; Edwards, W. B.; Anderson, C. J.; Welch, M. J. Reactivity of p-[1817] fluorophenacyl bromide for radiolabeling of protein and peptides. *Appl. Radiat. Isot.* 1997, 48, 907–916.

(46) Hansen, M. B.; Nielsen, S. E.; Berg, K. Reexamination and further development of a precise and rapid dye method for measuring cell growth/cell kill. *J. Immunol. Methods* 1989, 119, 203–210.

(47) Karlsson, R. Real-time competitive kinetic analysis of interactions between low-molecular-weight ligands in solution and surface-immobilized receptors. *Anal. Biochem.* 1994, 221, 142–151.

(48) Karlsson, R.; Stahlberg, R. Surface plasmon resonance detection and multispot sensing for direct monitoring of interactions involving low-molecular-weight analytes and for determination of low affinities. *Anal. Biochem.* 1995, 228, 274–280.

(49) Gomes, P.; Giralt, E.; Andreu, D. Surface plasmon resonance screening of synthetic peptides mimicking the immunodominant region of C-S8c1 foot-and-mouth disease virus. *Vaccine* 1999, 18, 362–370.

(50) Gomes, P.; Giralt, E.; Andreu, D. Direct single-step surface plasmon resonance analysis of interactions between small peptides and immobilized monoclonal antibodies. *J. Immunol. Methods* 2000, 235, 101–111.

(51) Ploug, M.; Ostergaard, S.; Hansen, L. B.; Holm, A.; Dano, K. Photoaffinity labeling of the human receptor for urokinase-type plasminogen activator using a decapeptide antagonist. Evidence for a composite ligand-binding site and a short interdomain separation. *Biochemistry* 1998, 37,3612–3622.

(52) Ohlson, S.; Strandh, M.; Nilshans, H. Detection and characterization of weak affinity antibody antigen recognition with biomolecular interaction analysis. *J. Mol. Recognit.* 1997, 10, 135–138.

(53) Piehler, J.; Brecht, A.; Gauglitz, G.; Maul, C.; Grabley, S.; et gal. Specific binding of low molecular weight ligands with direct optical detection. *Biosens. Bioelectron.* 1997, 12, 531–538.

(54) Markgren, P. O.; Hamalainen, M.; Danielson, U. H. Screening of compounds interacting with HIV-1 proteinase using optical biosensor technology. *Anal. Biochem.* 1998, 265, 340–350.

(55) Markgren, P. O.; Hamalainen, M.; Danielson, U. H. Kinetic analysis of the interaction between HIV-1 protease and inhibitors using optical biosensor technology. *Anal. Biochem.* 2000, 279, 71–78.

(56) Strandh, M.; Persson, B.; Roos, H.; Ohlson, S. Studies of interactions with weak affinities and low-molecular-weight compounds using surface plasmon resonance technology. *J. Mol. Recognit.* 1998, 11, 188–190.

(57) Malmqvist, M. BIACORE: an affinity biosensor system for characterization of biomolecular interactions. *Biochem. Soc. Trans.* 1999, 27, 335–340.

(58) Kampranis, S. C.; Gormley, N. A.; Tranter, R.; Orphanides, G.; Maxwell, A. Probing the binding of coumarins and cyclothialidines to DNA gyrase. *Biochemistry* 1999, 38, 1967–1976.

(59) Yamashita, D. S.; Smith, W. W.; Zhao, B.; Janson, C. A.; Tamoszek, T. A.; Bossard, M. J.; Levy, M. A.; Oh, H.-J.; Carr, T. J.; Thompson, S. K.; Ijames, C. F.; Carr, S. A.; McQueney, M.; D'Alessio, K. J.; Amegadzie, B. Y.; Hanning, C. R.; Abdel-Meguid, S.; DesJarlais, R. L.; Gleason, J. G.; Veber, D. F. Structure and design of potent and selective Cathepsin K Inhibitors. *J. Am. Chem. Soc.* 1997, 119, 11351–11352.

(60) Thompson, S. K.; Halbert, S. M.; Bossard, M. J.; Tomaszek, T. A.; Levy, M. A.; et al. Design of potent and selective human cathepsin K inhibitors that span the active site. *Proc. Natl. Acad. Sci. U.S.A.* 1997, 94,14249–14254.

(61) McGrath, M. E.; Klaus, J. L.; Barnes, M. G.; Bromine, D. Crystal structure of human cathepsin K com-

(61) plexed with a potent inhibitor [letter]. *Nat. Struct. BioL* 1997, 4, 105–109.

(62) Turk, D.; Podobnik, M; Popovic, T.; Katunuma, N.; Bode, W.; et al. Crystal structure of cathepsin B inhibited with CA030 at 2.0-A resolution: A basis for the design of specific epoxysuccinyl inhibitors. *Biochemistry* 1995, 34, 4791–4797.

(63) Yamamoto, D.; Matsumoto, K.; Ohishi, H.; Ishida, T.; Inoue, M.; et al. Refined X-ray structure of papain. E-64-complex at 2.1-A resolution. *J. Biol. Chem.* 1991, 266,14771–14777.

(64) Sautel, M.; Rudolf, K.; Wittneben, H.; Herzog, H.; Martinez, R.; et al. Neuropeptide Y and the nonpeptide antagonist BIBP 3226 share an overlapping binding site at the human Y1 receptor. *Mol. Pharmacol.* 1996, 50,285–292.

(65) Schwartz, T. W. Locating ligand-binding sites in 7TM receptors by protein engineering. *Curr. Opin. Biotechnol.* 1994, 5, 434–444.

(66) Ripka, A. S.; Rich, D. H. Peptidomimetic design. *Curr. Opin. Chem. Biol.* 1998, 2, 441–452.

(67) Meyer, E. F.; Botos, I.; Scapozza, L.; Zhang, D. Backward binding and other structural surprises. *Perspect. Drug Discovery Des.* 1995, 3, 168–195.

(68) Sheriff, D.; Silverton, E. W.; Padlan, E. A.; Cohen, G. H.; Smith-Gill, S. J.; et al. Three-dimensional structure of an antibody-antigen complex. *Proc. Natl. Acad. Sci. U.S.A.* 1987, 84,8075–8079.

(69) Padlan, E. A.; Silverton, E. W.; Sheriff, S.; Cohen, G. H.; Smith-Gill, S. J.; et al. Structure of an antibody-antigen complex: crystal structure of the HyHEL-10 Fab-lysozyme complex. *Proc. Natl. Acad. Sci. U.S.A.* 1989, 86, 5938–5942.

(70) Leysen, J. E.; Gommeren, W. The dissociation rate of unlabeled dopamine antagonists and agonists from the dopamine-D2 receptor, application of an original filter method. *J. Recept. Res.* 1984, 4, 817–845.

(71) Pargellis, C. A.; Morelock, M. M.; Graham, E. T.; Kinkade, P.; Pav, S.; et al. Determination of kinetic rate constants for the binding of inhibitors to HIV-1 protease and for the association and dissociation of active homodimer. *Biochemistry* 1994, 33, 12527-12534.

(72) Frieden, C.; Kurtz, L. C.; Gilbert, H. R. Adenosine deaminase and adenylate deamnase: comparative kinetic studies with transition state and ground-state analogue inhibitors. *Biochemistry* 1980, 19, 5303–5309.

(73) Gill, S. C.; von Hippel, P. H. Calculation of protein extinction coefficients from amino acid sequence data. *Anal. Biochem.* 1989, 182, 319–326.

(74) Abrams, M. J.; Juweid, M.; tenKate, C. I.; Schwartz, D. A.; Hauser, M. M.; Gaul, F. E.; Fuccello, A. J.; Rubin, R. H.; Strauss, H. W.; Fischman, A. J. Technetium-99m-human polyclonal IgG radiolabeled via the hydrazino nicotinamide derivative for imaging focal sites of infection in rats. *J Nucl Med* 1990, 31, 2022–2028.

(75) Lewis, M. R.; Raubitschek, A.; Shively, J. E. A facile, water-soluble method for modification of proteins with DOTA. Use of elevated temperature and optimized pH to achieve high specific activity and high chelate stability in radiolabeled immunoconjugates. *Bioconjug Chem* 1994, 5, 565–576.

TABLE 1

Summary of Biophysical Properties and Biological Activities for AHNP Analogs

| AHNP analogs | Composition | binding to HER2 | | | | |
|---|---|---|---|---|---|---|
| | | $k_{on} \times 10^2$ $M^{-1}$ $s^{-1}$ | $k_{off} \times 10^{-4}$ $s^{-1}$ | $K_D$ μM | % inhibition[a] | solubility[b] |
| 1 | FCDGFYACYMDV-NH2 | 14.10 | 4.53 | 0.32 | 35.5 | limited |
| 2 | FCDGFYACYMDV-OH | 9.90 | 6.43 | 0.65 | 22.3 | limited |
| 3 | YCDGFYACYMDV-NH2 | 19.60 | 2.94 | 0.15 | 59.6 | limited |
| 4 | dFCDGFYACdYMDV-NH2 | 17.20 | 6.03 | 0.35 | 26.0 | good |
| 5 | FCDGFYACYMDVK-NH2 | 6.17 | 5.12 | 0.83 | 20.0 | limited |
| 6 | FCDGFYACYKDV-OH | 2.19 | 12.50 | 5.70 | 8.4 | good |
| 7 | GFCDGFYACYMDV-OH | 11.10 | 8.08 | 0.73 | 15.8 | good |
| 8 | FCGDGFYACYMDV-OH | 9.22 | 7.01 | 0.76 | 18.4 | good |
| 9 | FCDGFYACYMDV-OH | 2.98 | 10.60 | 3.56 | 12.8 | good |

[a]Inhibition of T6-17 cell proliferation in MTT assays. Each value represents an average of at least four samples. Standard error did not exceed 535 for any of the studied analogues. [b]Peptide solubility is indicated as good if the peptide can be readily dissolved in the PBS buffer at 1 mg/mL, and as limited if pH adjustment is required for dissolving the peptide.

TABLE 2

Biodistribution of the $^{99m}$Tc labeled AHNP

| | $^{99m}$Tc-AHNP | |
|---|---|---|
| Organs N = 3 | ID %/g | Standard Deviation |
| Liver | 1.73 | 0.55 |
| Heart | 0.18 | 0.038 |
| Kidney | 8.6 | 3.0 |
| Lung | 0.39 | 0.12 |
| Spleen | 0.92 | 0.17 |
| Stomach | 1.8 | 0.25 |
| Small Intestine | 0.30 | 0.06 |
| Large Intestine | 0.46 | 0.29 |
| Muscle | 0.083 | 0.032 |
| Tumor | 0.24 | 0.050 |
| Blood | 0.59 | 0.15 |
| Tumor/Muscle | 3.0 | 0.64 |
| Tumor/Blood | 0.43 | 0.15 |

What is claimed:

1. An isolated peptide an amino acid sequence selected from the group consisting of:
YCDGFYACYMDV (SEQ ID NO:113);
FCDGFYACYKDV (SEQ ID NO:128);
dFCDGFYAGdYMDVK (SEQ ID NO:124);
GdFCDGFYACdYMDVK (SEQ ID NO:125);
GGdFCDGFYACdYMDVK (SEQ ID NO:126);
GGGdFCDGFYACdYMDVK (SEQ ID NO:127); and
dFCDGFYACDYMDV (SEQ ID NO:118).

2. A pharmaceutical composition comprising a peptide according to claim 1, and a pharmaceutically acceptable carrier or diluent.

3. A method of treating an individual who has cancer characterized by tumor cells that have a p185 on their cell surfaces comprising the steps of a) identifying said individual; b) administering to said individual, a therapeutically effective amount of a peptide having an amino acid sequence selected from the group consisting of:
YCDGFYACYMDV (SEQ ID NO: 113);
FCDGFYACYKDV (SEQ ID NO: 128);
dFCDGFYACdYMDVK (SEQ ID NO: 124);
GdFcDGFYACdYMDVK (SEQ ID NO: 125);
GGdFCDGFYACdYMDVK (SEQ ID NO: 126);
GGGdFCDGFYACdYMDVK (SEQ ID NO: 127); and
dFCDGFYACDYMDV (SEQ ID NO: 118)
in combination with a detectable agent and/or cytotoxic agent.

4. A composition comprising a conjugate of peptide linked to a detectable agent and/or cytotoxic agent, wherein the peptide has an amino acid sequence selected from the group consisting of:
YCDGFYACYMDV (SEQ ID NO:113);
FCDGFYACYKDV (SEQ ID NO:128);
dFCDGFYACdYMDVK (SEQ ID NO:124);
GdFCDGFYACdYMDVK (SEQ ID NO:125);
GGdFCDGFYACdYMDVK (SEQ ID NO:126);
GGGdFCDGFYACdYMDVK (SEQ ID NO:127); and
dFCDGFYACDYMDV (SEQ ID NO:118).

5. The composition of claim 4 wherein the peptide is linked to the detectable agent and/or the cytotoxic agent by a chelating linker.

6. The composition of claim 5 wherein the chelating linker is DOTA/DTPA.

7. The composition of claim 5 wherein said peptide is linked to a detectable agent.

8. The composition of claim 7 wherein said detectable agent is a radiosotope.

9. The composition of claim 8 wherein said radioisotope is selected from the group consisting of 99mTc, Y90, and 18F.

10. A method of detecting a tumor that has p185on tumor cell surfaces comprising the step of administering, to an individual suspected of having such a tumor or being susceptible to such a tumor, a composition comprising a conjugate of peptide linked to a detectable agent and/or cytotoxic agent, wherein the peptide has an amino acid sequence selected from the group consisting of:
YCDGFYACYMDV (SEQ ID NO: 113);
FCDGFYACYKDV (SEQ ID NO: 128);
dFCDGFYACdYMDVK (SEQ ID NO: 124);
GdFcDGFYACdYMDVK (SEQ ID NO: 125);
GGdFCDGFYACdYMDVK (SEQ ID NO: 126);
GGGdFCDGFYACdYMDVK (SEQ ID NO: 127); and
dFCDGFYACDYMDV (SEQ ID NO: 118) and detecting the presence of said conjugate, localized within the body of said individual.

11. The composition of claim 5, wherein said peptide is linked to a cytotoxic agent selected from the group consisting of: cytotoxic drugs, toxins and cytostatic drugs.

12. A pharmaceutical composition comprising a conjugated compound according to claim 4, and a pharmaceutically acceptable carrier or diluent.

13. A method of treating an individual who has cancer characterized by tumor cells that have a p185on their cell surfaces comprising the steps of:

a) identifying said individual;

b) administering to said individual, a therapeutically effective amount of composition comprising a conjugate of peptide linked to a detectable agent and/or cytotoxic agent, wherein the peptide has an amino acid sequence selected from the group consisting of:

YCDGFYACYMDV (SEQ ID NO: 113);
FCDGFYACYKDV (SEQ ID NO: 128);
dFCDGFYACdYMDVK (SEQ ID NO: 124);
GdFcDGFYACdYMDVK (SEQ ID NO: 125);
GGdFCDGFYACdYMDVK (SEQ ID NO: 126);
GGGdFCDGFYACdYMDVK (SEQ ID NO: 127); and
dFCDGFYACDYMDV (SEQ ID NO: 118).

14. The peptide of claim 1 wherein said peptide has the amino acid sequence:
YCDGFYACYMDV (SEQ ID NO:113).

15. The peptide of claim 1 wherein said peptide has the amino acid sequence:
FCDGFYACYKDV (SEQ ID NO:128).

16. The peptide of claim 1 wherein said peptide has the amino acid sequence:
dFCDGFYACdYMDVK (SEQ ID NO:124).

17. The peptide of claim 1 wherein said peptide has the amino acid sequence:
GdFCDGFYACdYMDVK (SEQ ID NO:125).

18. The peptide of claim 1 wherein said peptide has the amino acid sequence:
GGdFCDGFYACdYMDVK (SEQ ID NO:126).

19. The peptide of claim 1 wherein said peptide has the amino acid sequence:
GGGdFCDGFYACdYMDVK (SEQ ID NO:127).

20. The peptide of claim 1 wherein said peptide has the amino acid sequence:
dFCDGFYACDYMDV (SEQ ID NO:118).

21. The peptide according to any one of claims 15 and 16–20 wherein the carboxy terminus is amidated.

22. The peptide according to any one of claims 15 and 16–20 wherein the carboxy terminus is hydroxylated.

* * * * *